US012318130B2

(12) United States Patent
Viswanathan et al.

(10) Patent No.: US 12,318,130 B2
(45) Date of Patent: *Jun. 3, 2025

(54) SYSTEMS, APPARATUSES, AND METHODS FOR DELIVERY OF PULSED ELECTRIC FIELD ABLATIVE ENERGY TO ENDOCARDIAL TISSUE

(71) Applicant: Boston Scientific Scimed, Inc., Maple Grove, MN (US)

(72) Inventors: Raju Viswanathan, Mountain View, CA (US); Gary L. Long, Cincinnati, OH (US); Jean-Luc Pageard, Montreal (CA); Benoit Thibault, Coteau-du-Lac (CA)

(73) Assignee: Boston Scientific Scimed, Inc., Maple Grove, MN (US)

( * ) Notice: Subject to any disclaimer, the term of this patent is extended or adjusted under 35 U.S.C. 154(b) by 906 days.

This patent is subject to a terminal disclaimer.

(21) Appl. No.: 17/207,029

(22) Filed: Mar. 19, 2021

(65) Prior Publication Data

US 2022/0000546 A1     Jan. 6, 2022

Related U.S. Application Data

(63) Continuation of application No. PCT/US2019/051998, filed on Sep. 19, 2019.
(Continued)

(51) Int. Cl.
*A61B 18/14* (2006.01)
*A61B 5/00* (2006.01)
(Continued)

(52) U.S. Cl.
CPC .......... *A61B 18/1492* (2013.01); *A61B 5/287* (2021.01); *A61B 5/6853* (2013.01);
(Continued)

(58) Field of Classification Search
CPC ...... A61B 18/1492; A61B 2018/00083; A61B 2018/00196; A61B 2018/0022;
(Continued)

(56) References Cited

U.S. PATENT DOCUMENTS 4,200,104 A    4/1980 Harris
4,470,407 A    9/1984 Hussein
(Continued)

FOREIGN PATENT DOCUMENTS

EP    1042990 A1    10/2000
EP    1125549 A2    8/2001
(Continued)

OTHER PUBLICATIONS

Du Pre, B.C. et al., "Minimal coronary artery damage by myocardial electroporation ablation," Europace, 15(1):144-149 (2013).
(Continued)

*Primary Examiner* — Michael F Peffley
(74) *Attorney, Agent, or Firm* — Nelson Mullins Riley & Scarborough LLP

(57) ABSTRACT

Systems, devices, and methods for electroporation ablation therapy are disclosed herein, including an inflatable member for positioning an ablation device within a pulmonary vein ostium. An apparatus can include first and second shafts moveable relative to one another, first and second electrodes configured to generate an electric field for ablating tissue, and an inflatable member disposed between the first and second electrodes. In some embodiments, the inflatable member is configured to transition from an undeployed configuration to a deployed configuration in response to movement of the first and second shafts. In some embodiments, the inflatable member in the deployed configuration
(Continued)

can engage a wall of a pulmonary vein ostium and direct the electric field generated by the first and second electrodes toward the wall.

20 Claims, 23 Drawing Sheets

Related U.S. Application Data

(60) Provisional application No. 62/734,214, filed on Sep. 20, 2018.

(51) Int. Cl.
  *A61B 5/287* (2021.01)
  *A61B 18/00* (2006.01)

(52) U.S. Cl.
  CPC ........... *A61B 2018/00083* (2013.01); *A61B 2018/0022* (2013.01); *A61B 2018/00375* (2013.01); *A61B 2018/00577* (2013.01); *A61B 2018/00613* (2013.01); *A61B 2018/1467* (2013.01); *A61B 2018/1475* (2013.01)

(58) Field of Classification Search
  CPC .......... A61B 2018/00375; A61B 2018/00577; A61B 2018/00613; A61B 2018/1467; A61B 2018/1475; A61B 5/287; A61B 5/6853
  See application file for complete search history.

(56) References Cited

U.S. PATENT DOCUMENTS

| | | | |
|---|---|---|---|
| 4,739,759 A | 4/1988 | Rexroth et al. |
| 5,234,004 A | 8/1993 | Hascoet et al. |
| 5,242,441 A | 9/1993 | Avitall |
| 5,257,635 A | 11/1993 | Langberg |
| 5,281,213 A | 1/1994 | Milder et al. |
| 5,304,214 A | 4/1994 | Deford et al. |
| 5,306,296 A | 4/1994 | Wright et al. |
| 5,334,193 A | 8/1994 | Nardella |
| 5,341,807 A | 8/1994 | Nardella |
| 5,342,301 A | 8/1994 | Saab |
| 5,398,683 A | 3/1995 | Edwards et al. |
| 5,443,463 A | 8/1995 | Stern et al. |
| 5,454,370 A | 10/1995 | Avitall |
| 5,515,848 A | 5/1996 | Corbett et al. |
| 5,531,685 A | 7/1996 | Hemmer et al. |
| 5,545,161 A | 8/1996 | Imran |
| 5,578,040 A | 11/1996 | Smith |
| 5,617,854 A | 4/1997 | Munsif |
| 5,624,430 A | 4/1997 | Eton et al. |
| 5,667,491 A | 9/1997 | Pliquett et al. |
| 5,672,170 A | 9/1997 | Cho et al. |
| 5,700,243 A | 12/1997 | Narciso, Jr. |
| 5,702,438 A | 12/1997 | Avitall |
| 5,706,823 A | 1/1998 | Wodlinger |
| 5,722,400 A | 3/1998 | Ockuly et al. |
| 5,722,402 A | 3/1998 | Swanson et al. |
| 5,749,914 A | 5/1998 | Janssen |
| 5,779,699 A | 7/1998 | Lipson |
| 5,788,692 A | 8/1998 | Campbell et al. |
| 5,810,762 A | 9/1998 | Hofmann |
| 5,833,710 A | 11/1998 | Jacobson |
| 5,836,874 A | 11/1998 | Swanson et al. |
| 5,836,942 A | 11/1998 | Netherly et al. |
| 5,836,947 A | 11/1998 | Fleischman et al. |
| 5,843,154 A | 12/1998 | Osypka |
| 5,849,028 A | 12/1998 | Chen |
| 5,860,974 A * | 1/1999 | Abele .................... A61B 8/12 606/41 |
| 5,863,291 A | 1/1999 | Schaer |
| 5,868,736 A | 2/1999 | Swanson et al. |
| 5,871,523 A | 2/1999 | Fleischman et al. |
| 5,876,336 A | 3/1999 | Swanson et al. |
| 5,885,278 A | 3/1999 | Fleischman |
| 5,895,404 A | 4/1999 | Ruiz |
| 5,899,917 A | 5/1999 | Edwards et al. |
| 5,904,709 A | 5/1999 | Arndt et al. |
| 5,916,158 A | 6/1999 | Webster, Jr. |
| 5,916,213 A | 6/1999 | Haissaguerre et al. |
| 5,921,924 A | 7/1999 | Avitall |
| 5,928,269 A | 7/1999 | Alt |
| 5,928,270 A | 7/1999 | Ramsey, III |
| 5,938,660 A * | 8/1999 | Swartz ............... A61M 25/1011 606/45 |
| 6,002,955 A | 12/1999 | Willems et al. |
| 6,006,131 A | 12/1999 | Cooper et al. |
| 6,009,351 A | 12/1999 | Flachman |
| 6,014,579 A | 1/2000 | Pomeranz et al. |
| 6,029,671 A | 2/2000 | Stevens et al. |
| 6,033,403 A | 3/2000 | Tu et al. |
| 6,035,238 A | 3/2000 | Ingle et al. |
| 6,045,550 A | 4/2000 | Simpson et al. |
| 6,068,653 A | 5/2000 | LaFontaine |
| 6,071,274 A | 6/2000 | Thompson et al. |
| 6,071,281 A | 6/2000 | Burnside et al. |
| 6,074,389 A | 6/2000 | Levine et al. |
| 6,076,012 A | 6/2000 | Swanson et al. |
| 6,090,104 A | 7/2000 | Webster, Jr. |
| 6,096,036 A | 8/2000 | Bowe et al. |
| 6,113,595 A | 9/2000 | Muntermann |
| 6,119,041 A | 9/2000 | Pomeranz et al. |
| 6,120,500 A | 9/2000 | Bednarek et al. |
| 6,142,993 A | 11/2000 | Whayne et al. |
| 6,146,381 A | 11/2000 | Bowe et al. |
| 6,164,283 A | 12/2000 | Lesh |
| 6,167,291 A | 12/2000 | Barajas et al. |
| 6,171,305 B1 | 1/2001 | Sherman |
| 6,216,034 B1 | 4/2001 | Hofmann et al. |
| 6,219,582 B1 | 4/2001 | Hofstad et al. |
| 6,223,085 B1 | 4/2001 | Dann et al. |
| 6,231,518 B1 | 5/2001 | Grabek et al. |
| 6,245,064 B1 | 6/2001 | Lesh et al. |
| 6,251,107 B1 | 6/2001 | Schaer |
| 6,251,109 B1 * | 6/2001 | Hassett ............... A61B 18/1492 606/49 |
| 6,251,128 B1 | 6/2001 | Knopp et al. |
| 6,270,476 B1 | 8/2001 | Santoianni et al. |
| 6,272,384 B1 | 8/2001 | Simon et al. |
| 6,287,306 B1 | 9/2001 | Kroll et al. |
| 6,314,963 B1 | 11/2001 | Vaska et al. |
| 6,322,559 B1 | 11/2001 | Daulton et al. |
| 6,350,263 B1 | 2/2002 | Wetzig et al. |
| 6,370,412 B1 | 4/2002 | Armoundas et al. |
| 6,391,024 B1 | 5/2002 | Sun et al. |
| 6,447,505 B2 | 9/2002 | McGovern et al. |
| 6,464,699 B1 | 10/2002 | Swanson |
| 6,470,211 B1 | 10/2002 | Ideker et al. |
| 6,502,576 B1 | 1/2003 | Lesh |
| 6,503,247 B2 | 1/2003 | Swartz et al. |
| 6,517,534 B1 | 2/2003 | McGovern et al. |
| 6,527,724 B1 | 3/2003 | Fenici |
| 6,527,767 B2 | 3/2003 | Wang et al. |
| 6,592,581 B2 | 7/2003 | Bowe |
| 6,595,991 B2 | 7/2003 | Toellner et al. |
| 6,607,520 B2 | 8/2003 | Keane |
| 6,623,480 B1 | 9/2003 | Kuo et al. |
| 6,638,278 B2 | 10/2003 | Falwell et al. |
| 6,666,863 B2 | 12/2003 | Wentzel et al. |
| 6,669,693 B2 | 12/2003 | Friedman |
| 6,702,811 B2 | 3/2004 | Stewart et al. |
| 6,719,756 B1 | 4/2004 | Muntermann |
| 6,723,092 B2 | 4/2004 | Brown et al. |
| 6,728,563 B2 | 4/2004 | Rashidi |
| 6,743,225 B2 | 6/2004 | Sanchez et al. |
| 6,743,226 B2 | 6/2004 | Cosman et al. |
| 6,743,239 B1 | 6/2004 | Kuehn et al. |
| 6,764,486 B2 | 7/2004 | Natale |
| 6,780,181 B2 | 8/2004 | Kroll et al. |
| 6,805,128 B1 | 10/2004 | Pless et al. |
| 6,807,447 B2 | 10/2004 | Griffin, III |
| 6,892,091 B1 | 5/2005 | Ben-Haim et al. |

(56) References Cited

U.S. PATENT DOCUMENTS

| | | |
|---|---|---|
| 6,893,438 B2 | 5/2005 | Hall et al. |
| 6,926,714 B1 | 8/2005 | Sra |
| 6,955,173 B2 | 10/2005 | Lesh |
| 6,960,206 B2 | 11/2005 | Keane |
| 6,960,207 B2 | 11/2005 | Vanney et al. |
| 6,972,016 B2 | 12/2005 | Hill et al. |
| 6,973,339 B2 | 12/2005 | Govari |
| 6,979,331 B2 | 12/2005 | Hintringer et al. |
| 6,984,232 B2 | 1/2006 | Vanney et al. |
| 6,985,776 B2 | 1/2006 | Kane et al. |
| 7,001,383 B2 | 2/2006 | Keidar |
| 7,041,095 B2 | 5/2006 | Wang et al. |
| 7,113,831 B2 | 9/2006 | Hooven |
| 7,171,263 B2 | 1/2007 | Darvish et al. |
| 7,182,725 B2 | 2/2007 | Bonan et al. |
| 7,195,628 B2 | 3/2007 | Falkenberg |
| 7,207,988 B2 | 4/2007 | Leckrone et al. |
| 7,207,989 B2 | 4/2007 | Pike et al. |
| 7,229,402 B2 | 6/2007 | Diaz et al. |
| 7,229,437 B2 | 6/2007 | Johnson et al. |
| 7,250,049 B2 | 7/2007 | Roop et al. |
| 7,285,116 B2 | 10/2007 | De et al. |
| 7,285,119 B2 | 10/2007 | Stewart et al. |
| 7,326,208 B2 | 2/2008 | Vanney et al. |
| 7,346,379 B2 | 3/2008 | Eng et al. |
| 7,367,974 B2 | 5/2008 | Haemmerich et al. |
| 7,374,567 B2 | 5/2008 | Heuser |
| 7,387,629 B2 | 6/2008 | Vanney et al. |
| 7,387,630 B2 | 6/2008 | Mest |
| 7,387,636 B2 | 6/2008 | Cohn et al. |
| 7,416,552 B2 | 8/2008 | Paul et al. |
| 7,419,477 B2 | 9/2008 | Simpson et al. |
| 7,419,489 B2 | 9/2008 | Vanney et al. |
| 7,422,591 B2 | 9/2008 | Phan |
| 7,429,261 B2 | 9/2008 | Kunis et al. |
| 7,435,248 B2 | 10/2008 | Taimisto et al. |
| 7,513,896 B2 | 4/2009 | Orszulak |
| 7,527,625 B2 | 5/2009 | Knight et al. |
| 7,578,816 B2 | 8/2009 | Boveja et al. |
| 7,588,567 B2 | 9/2009 | Boveja et al. |
| 7,623,899 B2 | 11/2009 | Worley et al. |
| 7,678,108 B2 | 3/2010 | Chrisitian et al. |
| 7,681,579 B2 | 3/2010 | Schwartz |
| 7,771,421 B2 | 8/2010 | Stewart et al. |
| 7,805,182 B2 | 9/2010 | Weese et al. |
| 7,842,031 B2 * | 11/2010 | Abboud ............... A61B 5/0537 606/22 |
| 7,850,642 B2 | 12/2010 | Moll et al. |
| 7,850,685 B2 | 12/2010 | Kunis et al. |
| 7,857,808 B2 | 12/2010 | Oral et al. |
| 7,857,809 B2 | 12/2010 | Drysen |
| 7,869,865 B2 | 1/2011 | Govari et al. |
| 7,896,873 B2 | 3/2011 | Hiller et al. |
| 7,917,211 B2 | 3/2011 | Zacouto |
| 7,918,819 B2 | 4/2011 | Karmarkar et al. |
| 7,918,850 B2 | 4/2011 | Govari et al. |
| 7,922,714 B2 | 4/2011 | Stevens-Wright |
| 7,955,827 B2 | 6/2011 | Rubinsky et al. |
| 8,048,067 B2 | 11/2011 | Davalos et al. |
| 8,048,072 B2 | 11/2011 | Verin et al. |
| 8,100,895 B2 | 1/2012 | Panos et al. |
| 8,100,900 B2 | 1/2012 | Prinz et al. |
| 8,108,069 B2 | 1/2012 | Stahler et al. |
| 8,133,220 B2 | 3/2012 | Lee et al. |
| 8,137,342 B2 | 3/2012 | Crossman |
| 8,145,289 B2 | 3/2012 | Calabro' et al. |
| 8,147,486 B2 | 4/2012 | Honour et al. |
| 8,160,690 B2 | 4/2012 | Wilfley et al. |
| 8,175,680 B2 | 5/2012 | Panescu |
| 8,182,477 B2 | 5/2012 | Orszulak et al. |
| 8,206,384 B2 | 6/2012 | Falwell et al. |
| 8,206,385 B2 | 6/2012 | Stangenes et al. |
| 8,216,221 B2 | 7/2012 | Ibrahim et al. |
| 8,221,411 B2 | 7/2012 | Francischelli et al. |
| 8,226,648 B2 | 7/2012 | Paul et al. |
| 8,228,065 B2 | 7/2012 | Wirtz et al. |
| 8,235,986 B2 | 8/2012 | Kulesa et al. |
| 8,235,988 B2 | 8/2012 | Davis et al. |
| 8,251,986 B2 | 8/2012 | Chornenky et al. |
| 8,282,631 B2 | 10/2012 | Davalos et al. |
| 8,287,532 B2 | 10/2012 | Carroll et al. |
| 8,414,508 B2 | 4/2013 | Thapliyal et al. |
| 8,430,875 B2 | 4/2013 | Ibrahim et al. |
| 8,433,394 B2 | 4/2013 | Harlev et al. |
| 8,449,535 B2 | 5/2013 | Deno et al. |
| 8,454,594 B2 | 6/2013 | Demarais et al. |
| 8,463,368 B2 | 6/2013 | Harlev et al. |
| 8,475,450 B2 | 7/2013 | Govari et al. |
| 8,486,063 B2 | 7/2013 | Werneth et al. |
| 8,500,733 B2 | 8/2013 | Watson |
| 8,535,304 B2 | 9/2013 | Sklar et al. |
| 8,538,501 B2 | 9/2013 | Venkatachalam et al. |
| 8,562,588 B2 | 10/2013 | Hobbs et al. |
| 8,568,406 B2 | 10/2013 | Harlev et al. |
| 8,571,635 B2 | 10/2013 | McGee |
| 8,571,647 B2 | 10/2013 | Harlev et al. |
| 8,585,695 B2 | 11/2013 | Shih |
| 8,588,885 B2 | 11/2013 | Hall et al. |
| 8,597,288 B2 | 12/2013 | Christian |
| 8,608,735 B2 | 12/2013 | Govari et al. |
| 8,628,522 B2 | 1/2014 | Ibrahim et al. |
| 8,632,534 B2 | 1/2014 | Pearson et al. |
| 8,647,338 B2 | 2/2014 | Chornenky et al. |
| 8,708,952 B2 | 4/2014 | Cohen et al. |
| 8,734,442 B2 | 5/2014 | Cao et al. |
| 8,771,267 B2 | 7/2014 | Kunis et al. |
| 8,795,310 B2 | 8/2014 | Fung et al. |
| 8,808,273 B2 | 8/2014 | Caples et al. |
| 8,808,281 B2 | 8/2014 | Emmons et al. |
| 8,834,461 B2 | 9/2014 | Werneth et al. |
| 8,834,464 B2 | 9/2014 | Stewart et al. |
| 8,868,169 B2 | 10/2014 | Narayan et al. |
| 8,876,817 B2 | 11/2014 | Avitall et al. |
| 8,880,195 B2 | 11/2014 | Azure |
| 8,886,309 B2 | 11/2014 | Luther et al. |
| 8,903,488 B2 | 12/2014 | Callas et al. |
| 8,920,411 B2 | 12/2014 | Gelbart et al. |
| 8,926,589 B2 | 1/2015 | Govari |
| 8,932,287 B2 | 1/2015 | Gelbart et al. |
| 8,945,117 B2 | 2/2015 | Bencini |
| 8,979,841 B2 | 3/2015 | Kunis et al. |
| 8,986,278 B2 | 3/2015 | Fung et al. |
| 9,002,442 B2 | 4/2015 | Harley et al. |
| 9,005,189 B2 | 4/2015 | Davalos et al. |
| 9,005,194 B2 | 4/2015 | Oral et al. |
| 9,011,425 B2 | 4/2015 | Fischer et al. |
| 9,044,245 B2 | 6/2015 | Condie et al. |
| 9,055,959 B2 | 6/2015 | Vaska et al. |
| 9,072,518 B2 | 7/2015 | Swanson |
| 9,078,667 B2 | 7/2015 | Besser et al. |
| 9,101,374 B1 | 8/2015 | Hoch et al. |
| 9,113,911 B2 | 8/2015 | Sherman |
| 9,119,533 B2 | 9/2015 | Ghaffari |
| 9,119,634 B2 | 9/2015 | Gelbart et al. |
| 9,131,897 B2 | 9/2015 | Harada et al. |
| 9,155,590 B2 | 10/2015 | Mathur |
| 9,162,037 B2 | 10/2015 | Belson et al. |
| 9,179,972 B2 | 11/2015 | Olson |
| 9,186,481 B2 | 11/2015 | Avitall et al. |
| 9,192,769 B2 | 11/2015 | Donofrio et al. |
| 9,204,916 B2 | 12/2015 | Lalonde |
| 9,211,405 B2 | 12/2015 | Mahapatra et al. |
| 9,216,055 B2 | 12/2015 | Spence et al. |
| 9,233,248 B2 | 1/2016 | Luther et al. |
| 9,237,926 B2 | 1/2016 | Nollert et al. |
| 9,262,252 B2 | 2/2016 | Kirkpatrick et al. |
| 9,277,957 B2 | 3/2016 | Long et al. |
| 9,282,910 B2 | 3/2016 | Narayan et al. |
| 9,289,258 B2 | 3/2016 | Cohen |
| 9,289,606 B2 | 3/2016 | Paul et al. |
| 9,295,516 B2 | 3/2016 | Pearson et al. |
| 9,301,801 B2 | 4/2016 | Scheib |
| 9,375,268 B2 | 6/2016 | Long |
| 9,387,031 B2 | 7/2016 | Stewart et al. |

(56) References Cited

U.S. PATENT DOCUMENTS

| | | |
|---|---|---|
| 9,414,881 B2 | 8/2016 | Callas et al. |
| 9,468,495 B2 | 10/2016 | Kunis et al. |
| 9,474,486 B2 | 10/2016 | Eliason et al. |
| 9,474,574 B2 | 10/2016 | Ibrahim et al. |
| 9,480,525 B2 | 11/2016 | Lopes et al. |
| 9,486,272 B2 | 11/2016 | Bonyak et al. |
| 9,486,273 B2 | 11/2016 | Lopes et al. |
| 9,492,227 B2 | 11/2016 | Lopes et al. |
| 9,492,228 B2 | 11/2016 | Lopes et al. |
| 9,510,888 B2 | 12/2016 | Lalonde |
| 9,517,103 B2 | 12/2016 | Panescu et al. |
| 9,526,573 B2 | 12/2016 | Lopes et al. |
| 9,532,831 B2 | 1/2017 | Reinders et al. |
| 9,539,010 B2 | 1/2017 | Gagner et al. |
| 9,554,848 B2 | 1/2017 | Stewart et al. |
| 9,554,851 B2 | 1/2017 | Sklar et al. |
| 9,700,368 B2 | 7/2017 | Callas et al. |
| 9,724,170 B2 | 8/2017 | Mickelsen |
| 9,757,193 B2 | 9/2017 | Zarins et al. |
| 9,782,099 B2 | 10/2017 | Williams et al. |
| 9,795,442 B2 | 10/2017 | Salahieh et al. |
| 9,801,681 B2 | 10/2017 | Laske et al. |
| 9,808,304 B2 | 11/2017 | Lalonde |
| 9,861,802 B2 | 1/2018 | Mickelsen |
| 9,913,685 B2 | 3/2018 | Clark et al. |
| 9,931,487 B2 | 4/2018 | Quinn et al. |
| 9,987,081 B1 | 6/2018 | Bowers et al. |
| 9,999,465 B2 | 6/2018 | Long et al. |
| 10,010,368 B2 | 7/2018 | Laske et al. |
| 10,016,232 B1 | 7/2018 | Bowers et al. |
| 10,130,423 B1 | 11/2018 | Viswanathan et al. |
| 10,172,673 B2 | 1/2019 | Viswanathan et al. |
| 10,194,818 B2 | 2/2019 | Williams et al. |
| 10,285,755 B2 | 5/2019 | Stewart et al. |
| 10,322,286 B2 | 6/2019 | Viswanathan et al. |
| 10,433,906 B2 | 10/2019 | Mickelsen |
| 10,433,908 B2 | 10/2019 | Viswanathan et al. |
| 10,512,505 B2 | 12/2019 | Viswanathan |
| 10,512,779 B2 | 12/2019 | Viswanathan et al. |
| 10,517,672 B2 | 12/2019 | Long |
| 10,687,892 B2 * | 6/2020 | Long .................. A61B 5/6853 |
| 2001/0000791 A1 | 5/2001 | Suorsa et al. |
| 2001/0007070 A1 | 7/2001 | Stewart et al. |
| 2001/0016724 A1 | 8/2001 | Davis et al. |
| 2001/0044624 A1 | 11/2001 | Seraj et al. |
| 2002/0052602 A1 | 5/2002 | Wang et al. |
| 2002/0077627 A1 | 6/2002 | Johnson et al. |
| 2002/0087169 A1 | 7/2002 | Brock et al. |
| 2002/0091384 A1 | 7/2002 | Hooven et al. |
| 2002/0095176 A1 | 7/2002 | Prestel |
| 2002/0111618 A1 | 8/2002 | Stewart et al. |
| 2002/0156526 A1 | 10/2002 | Hlavka et al. |
| 2002/0161323 A1 | 10/2002 | Miller et al. |
| 2002/0169445 A1 | 11/2002 | Jain et al. |
| 2002/0177765 A1 | 11/2002 | Bowe et al. |
| 2002/0183638 A1 | 12/2002 | Swanson |
| 2003/0014098 A1 | 1/2003 | Quijano et al. |
| 2003/0018374 A1 | 1/2003 | Paulos |
| 2003/0023287 A1 | 1/2003 | Edwards et al. |
| 2003/0028189 A1 | 2/2003 | Woloszko et al. |
| 2003/0050637 A1 | 3/2003 | Maguire et al. |
| 2003/0114849 A1 | 6/2003 | Ryan |
| 2003/0125729 A1 | 7/2003 | Hooven et al. |
| 2003/0130598 A1 | 7/2003 | Manning et al. |
| 2003/0130711 A1 | 7/2003 | Pearson et al. |
| 2003/0204161 A1 | 10/2003 | Ferek-Petric |
| 2003/0229379 A1 | 12/2003 | Maynard |
| 2004/0039382 A1 | 2/2004 | Kroll et al. |
| 2004/0049181 A1 | 3/2004 | Stewart et al. |
| 2004/0049182 A1 | 3/2004 | Koblish et al. |
| 2004/0082859 A1 | 4/2004 | Schaer |
| 2004/0082948 A1 | 4/2004 | Stewart et al. |
| 2004/0087939 A1 | 5/2004 | Eggers et al. |
| 2004/0111087 A1 | 6/2004 | Stern et al. |
| 2004/0199157 A1 | 10/2004 | Palanker et al. |
| 2004/0231683 A1 | 11/2004 | Eng et al. |
| 2004/0236360 A1 | 11/2004 | Cohn et al. |
| 2004/0254607 A1 | 12/2004 | Wittenberger et al. |
| 2004/0267337 A1 | 12/2004 | Hayzelden |
| 2005/0033282 A1 | 2/2005 | Hooven |
| 2005/0187545 A1 | 8/2005 | Hooven et al. |
| 2005/0222632 A1 | 10/2005 | Obino |
| 2005/0251130 A1 | 11/2005 | Boveja et al. |
| 2005/0261672 A1 | 11/2005 | Deem et al. |
| 2006/0009755 A1 | 1/2006 | Sra |
| 2006/0009759 A1 | 1/2006 | Chrisitian et al. |
| 2006/0015095 A1 | 1/2006 | Desinger et al. |
| 2006/0015165 A1 | 1/2006 | Bertolero et al. |
| 2006/0024359 A1 | 2/2006 | Walker et al. |
| 2006/0058781 A1 | 3/2006 | Long |
| 2006/0111702 A1 | 5/2006 | Oral et al. |
| 2006/0142801 A1* | 6/2006 | Demarais .................. A61N 1/40 607/2 |
| 2006/0167448 A1 | 7/2006 | Kozel |
| 2006/0217703 A1 | 9/2006 | Chornenky et al. |
| 2006/0241734 A1 | 10/2006 | Marshall et al. |
| 2006/0264752 A1 | 11/2006 | Rubinsky et al. |
| 2006/0270900 A1 | 11/2006 | Chin et al. |
| 2006/0287648 A1 | 12/2006 | Schwartz |
| 2006/0293730 A1 | 12/2006 | Rubinsky et al. |
| 2006/0293731 A1 | 12/2006 | Rubinsky et al. |
| 2007/0005053 A1 | 1/2007 | Dando |
| 2007/0021744 A1 | 1/2007 | Creighton |
| 2007/0060989 A1 | 3/2007 | Deem et al. |
| 2007/0066972 A1 | 3/2007 | Ormsby et al. |
| 2007/0083194 A1 | 4/2007 | Kunis et al. |
| 2007/0129721 A1 | 6/2007 | Phan et al. |
| 2007/0129760 A1 | 6/2007 | Demarais et al. |
| 2007/0156135 A1 | 7/2007 | Rubinsky et al. |
| 2007/0167740 A1 | 7/2007 | Grunewald et al. |
| 2007/0167940 A1 | 7/2007 | Stevens-Wright |
| 2007/0173878 A1 | 7/2007 | Heuser |
| 2007/0208329 A1 | 9/2007 | Ward et al. |
| 2007/0225589 A1 | 9/2007 | Viswanathan |
| 2007/0249923 A1 | 10/2007 | Keenan |
| 2007/0260223 A1 | 11/2007 | Scheibe et al. |
| 2007/0270792 A1 | 11/2007 | Hennemann et al. |
| 2008/0009855 A1 | 1/2008 | Hamou |
| 2008/0033426 A1 | 2/2008 | Machell |
| 2008/0065061 A1 | 3/2008 | Viswanathan |
| 2008/0086120 A1 | 4/2008 | Mirza et al. |
| 2008/0091195 A1 | 4/2008 | Sliwa et al. |
| 2008/0103545 A1 | 5/2008 | Bolea et al. |
| 2008/0132885 A1 | 6/2008 | Rubinsky et al. |
| 2008/0161789 A1 | 7/2008 | Thao et al. |
| 2008/0172048 A1 | 7/2008 | Martin et al. |
| 2008/0200913 A1 | 8/2008 | Viswanathan |
| 2008/0208118 A1 | 8/2008 | Goldman |
| 2008/0243214 A1 | 10/2008 | Koblish |
| 2008/0281322 A1 | 11/2008 | Sherman et al. |
| 2008/0300574 A1 | 12/2008 | Belson et al. |
| 2008/0300588 A1 | 12/2008 | Groth et al. |
| 2009/0024084 A1 | 1/2009 | Khosla et al. |
| 2009/0048591 A1 | 2/2009 | Ibrahim et al. |
| 2009/0062788 A1 | 3/2009 | Long et al. |
| 2009/0076500 A1 | 3/2009 | Azure |
| 2009/0105654 A1 | 4/2009 | Kurth et al. |
| 2009/0138009 A1 | 5/2009 | Viswanathan et al. |
| 2009/0149917 A1 | 6/2009 | Whitehurst et al. |
| 2009/0163905 A1 | 6/2009 | Winkler et al. |
| 2009/0228003 A1 | 9/2009 | Sinelnikov |
| 2009/0240248 A1 | 9/2009 | Deford et al. |
| 2009/0275827 A1 | 11/2009 | Aiken et al. |
| 2009/0281477 A1 | 11/2009 | Mikus et al. |
| 2009/0306651 A1 | 12/2009 | Schneider |
| 2010/0004623 A1 | 1/2010 | Hamilton et al. |
| 2010/0023004 A1 | 1/2010 | Francischelli et al. |
| 2010/0137861 A1 | 6/2010 | Soroff et al. |
| 2010/0185140 A1 | 7/2010 | Kassab et al. |
| 2010/0185186 A1 | 7/2010 | Longoria |
| 2010/0191112 A1 | 7/2010 | Demarais et al. |
| 2010/0191232 A1 | 7/2010 | Boveda |
| 2010/0241185 A1 | 9/2010 | Mahapatra et al. |
| 2010/0261994 A1 | 10/2010 | Davalos et al. |

(56) References Cited

U.S. PATENT DOCUMENTS

| | | |
|---|---|---|
| 2010/0274238 A1 | 10/2010 | Klimovitch |
| 2010/0280513 A1 | 11/2010 | Juergen et al. |
| 2010/0280539 A1 | 11/2010 | Miyoshi et al. |
| 2010/0292687 A1 | 11/2010 | Kauphusman et al. |
| 2010/0312096 A1 | 12/2010 | Guttman et al. |
| 2010/0312300 A1 | 12/2010 | Ryu et al. |
| 2011/0028962 A1 | 2/2011 | Werneth et al. |
| 2011/0028964 A1 | 2/2011 | Edwards |
| 2011/0040199 A1 | 2/2011 | Hopenfeld |
| 2011/0098694 A1 | 4/2011 | Long |
| 2011/0106221 A1 | 5/2011 | Neal et al. |
| 2011/0130708 A1 | 6/2011 | Perry et al. |
| 2011/0144524 A1 | 6/2011 | Fish et al. |
| 2011/0144633 A1 | 6/2011 | Govari |
| 2011/0160785 A1 | 6/2011 | Mori et al. |
| 2011/0190659 A1 | 8/2011 | Long et al. |
| 2011/0190727 A1 | 8/2011 | Edmunds et al. |
| 2011/0213231 A1 | 9/2011 | Hall et al. |
| 2011/0276047 A1 | 11/2011 | Sklar et al. |
| 2011/0276075 A1 | 11/2011 | Fung et al. |
| 2011/0288544 A1 | 11/2011 | Verin et al. |
| 2011/0288547 A1 | 11/2011 | Morgan et al. |
| 2011/0313417 A1 | 12/2011 | De et al. |
| 2012/0029512 A1 | 2/2012 | Willard et al. |
| 2012/0046570 A1 | 2/2012 | Villegas et al. |
| 2012/0053581 A1 | 3/2012 | Wittkampf et al. |
| 2012/0059255 A1 | 3/2012 | Paul et al. |
| 2012/0071872 A1 | 3/2012 | Rubinsky et al. |
| 2012/0078320 A1 | 3/2012 | Schotzko et al. |
| 2012/0078343 A1 | 3/2012 | Fish |
| 2012/0089089 A1 | 4/2012 | Swain et al. |
| 2012/0095459 A1 | 4/2012 | Callas et al. |
| 2012/0101413 A1 | 4/2012 | Beetel et al. |
| 2012/0158021 A1 | 6/2012 | Morrill |
| 2012/0165667 A1 | 6/2012 | Altmann et al. |
| 2012/0172859 A1 | 7/2012 | Condie et al. |
| 2012/0172867 A1 | 7/2012 | Ryu et al. |
| 2012/0197100 A1 | 8/2012 | Razavi et al. |
| 2012/0209260 A1 | 8/2012 | Lambert et al. |
| 2012/0220998 A1 | 8/2012 | Long et al. |
| 2012/0265198 A1 | 10/2012 | Crow et al. |
| 2012/0283582 A1 | 11/2012 | Mahapatra et al. |
| 2012/0303019 A1 | 11/2012 | Zhao et al. |
| 2012/0310052 A1 | 12/2012 | Mahapatra et al. |
| 2012/0310230 A1 | 12/2012 | Willis |
| 2012/0310237 A1 | 12/2012 | Swanson |
| 2012/0316557 A1 | 12/2012 | Sartor et al. |
| 2013/0030430 A1 | 1/2013 | Stewart et al. |
| 2013/0060247 A1 | 3/2013 | Sklar et al. |
| 2013/0060248 A1 | 3/2013 | Sklar et al. |
| 2013/0079768 A1 | 3/2013 | De et al. |
| 2013/0090651 A1 | 4/2013 | Smith |
| 2013/0096655 A1 | 4/2013 | Moffitt et al. |
| 2013/0103027 A1 | 4/2013 | Sklar et al. |
| 2013/0103064 A1 | 4/2013 | Arenson et al. |
| 2013/0131662 A1 | 5/2013 | Wittkampf |
| 2013/0158538 A1 | 6/2013 | Govari |
| 2013/0158621 A1 | 6/2013 | Ding et al. |
| 2013/0172715 A1 | 7/2013 | Just et al. |
| 2013/0172864 A1 | 7/2013 | Ibrahim et al. |
| 2013/0172875 A1 | 7/2013 | Govari et al. |
| 2013/0184702 A1 | 7/2013 | Neal et al. |
| 2013/0218157 A1 | 8/2013 | Callas et al. |
| 2013/0226174 A1 | 8/2013 | Ibrahim et al. |
| 2013/0237984 A1 | 9/2013 | Sklar |
| 2013/0253415 A1 | 9/2013 | Sano et al. |
| 2013/0296679 A1 | 11/2013 | Condie et al. |
| 2013/0310829 A1 | 11/2013 | Cohen |
| 2013/0317385 A1 | 11/2013 | Sklar et al. |
| 2013/0331831 A1 | 12/2013 | Werneth et al. |
| 2013/0338467 A1 | 12/2013 | Grasse et al. |
| 2014/0005664 A1 | 1/2014 | Govari et al. |
| 2014/0024911 A1 | 1/2014 | Harlev et al. |
| 2014/0039288 A1 | 2/2014 | Hue-Teh |
| 2014/0051993 A1 | 2/2014 | McGee |
| 2014/0052118 A1 | 2/2014 | Laske et al. |
| 2014/0052126 A1 | 2/2014 | Long et al. |
| 2014/0052216 A1 | 2/2014 | Long et al. |
| 2014/0058377 A1 | 2/2014 | Deem et al. |
| 2014/0081113 A1 | 3/2014 | Cohen et al. |
| 2014/0100563 A1 | 4/2014 | Govari et al. |
| 2014/0107644 A1 | 4/2014 | Falwell et al. |
| 2014/0142408 A1 | 5/2014 | De et al. |
| 2014/0148804 A1 | 5/2014 | Ward et al. |
| 2014/0163480 A1 | 6/2014 | Govari et al. |
| 2014/0163546 A1 | 6/2014 | Govari et al. |
| 2014/0171942 A1 | 6/2014 | Werneth et al. |
| 2014/0180035 A1 | 6/2014 | Anderson |
| 2014/0187916 A1 | 7/2014 | Clark et al. |
| 2014/0194716 A1 | 7/2014 | Diep et al. |
| 2014/0194867 A1 | 7/2014 | Fish et al. |
| 2014/0200567 A1 | 7/2014 | Cox et al. |
| 2014/0235986 A1 | 8/2014 | Harlev et al. |
| 2014/0235988 A1 | 8/2014 | Ghosh |
| 2014/0235989 A1 | 8/2014 | Wodlinger et al. |
| 2014/0243851 A1 | 8/2014 | Cohen et al. |
| 2014/0276760 A1 | 9/2014 | Bonyak et al. |
| 2014/0276782 A1 | 9/2014 | Paskar |
| 2014/0276791 A1 | 9/2014 | Ku et al. |
| 2014/0288556 A1 | 9/2014 | Ibrahim et al. |
| 2014/0303721 A1 | 10/2014 | Fung et al. |
| 2014/0343549 A1 | 11/2014 | Spear et al. |
| 2014/0364845 A1 | 12/2014 | Rashidi |
| 2014/0371613 A1 | 12/2014 | Narayan et al. |
| 2015/0005767 A1 | 1/2015 | Werneth et al. |
| 2015/0011995 A1 | 1/2015 | Avitall et al. |
| 2015/0066108 A1 | 3/2015 | Shi et al. |
| 2015/0119674 A1 | 4/2015 | Fischell et al. |
| 2015/0126840 A1 | 5/2015 | Thakur et al. |
| 2015/0133914 A1 | 5/2015 | Koblish |
| 2015/0138977 A1 | 5/2015 | Dacosta |
| 2015/0141978 A1 | 5/2015 | Subramaniam et al. |
| 2015/0141982 A1 | 5/2015 | Lee |
| 2015/0142041 A1 | 5/2015 | Kendale et al. |
| 2015/0148796 A1 | 5/2015 | Bencini |
| 2015/0150472 A1 | 6/2015 | Harlev et al. |
| 2015/0157402 A1 | 6/2015 | Kunis et al. |
| 2015/0157412 A1 | 6/2015 | Wallace et al. |
| 2015/0164584 A1 | 6/2015 | Davalos et al. |
| 2015/0173824 A1 | 6/2015 | Davalos et al. |
| 2015/0173828 A1 | 6/2015 | Avitall |
| 2015/0174404 A1 | 6/2015 | Rousso et al. |
| 2015/0182740 A1 | 7/2015 | Mickelsen |
| 2015/0196217 A1 | 7/2015 | Harlev et al. |
| 2015/0223726 A1 | 8/2015 | Harlev et al. |
| 2015/0230699 A1 | 8/2015 | Berul et al. |
| 2015/0258344 A1 | 9/2015 | Tandri et al. |
| 2015/0265342 A1 | 9/2015 | Long et al. |
| 2015/0265344 A1 | 9/2015 | Aktas et al. |
| 2015/0272656 A1 | 10/2015 | Chen |
| 2015/0272664 A9 | 10/2015 | Cohen |
| 2015/0272667 A1 | 10/2015 | Govari et al. |
| 2015/0282729 A1 | 10/2015 | Harlev et al. |
| 2015/0289923 A1 | 10/2015 | Davalos et al. |
| 2015/0304879 A1 | 10/2015 | Dacosta |
| 2015/0320481 A1 | 11/2015 | Cosman et al. |
| 2015/0321021 A1 | 11/2015 | Tandri et al. |
| 2015/0342532 A1 | 12/2015 | Basu et al. |
| 2015/0343212 A1 | 12/2015 | Rousso et al. |
| 2015/0351836 A1 | 12/2015 | Prutchi |
| 2015/0359583 A1 | 12/2015 | Swanson |
| 2016/0000500 A1 | 1/2016 | Salahieh et al. |
| 2016/0008061 A1 | 1/2016 | Fung et al. |
| 2016/0008065 A1 | 1/2016 | Gliner et al. |
| 2016/0029960 A1 | 2/2016 | Toth et al. |
| 2016/0038772 A1 | 2/2016 | Thapliyal et al. |
| 2016/0051204 A1 | 2/2016 | Harlev et al. |
| 2016/0051324 A1 | 2/2016 | Stewart et al. |
| 2016/0058493 A1 | 3/2016 | Neal et al. |
| 2016/0058506 A1 | 3/2016 | Spence et al. |
| 2016/0066993 A1 | 3/2016 | Avitall et al. |
| 2016/0074679 A1 | 3/2016 | Thapliyal et al. |
| 2016/0095531 A1 | 4/2016 | Narayan et al. |
| 2016/0095642 A1 | 4/2016 | Deno et al. |

(56) References Cited

U.S. PATENT DOCUMENTS

| | | |
|---|---|---|
| 2016/0095653 A1 | 4/2016 | Lambert et al. |
| 2016/0100797 A1 | 4/2016 | Mahapatra et al. |
| 2016/0100884 A1 | 4/2016 | Fay et al. |
| 2016/0106498 A1 | 4/2016 | Highsmith et al. |
| 2016/0106500 A1 | 4/2016 | Olson |
| 2016/0113709 A1 | 4/2016 | Maor |
| 2016/0113712 A1 | 4/2016 | Cheung et al. |
| 2016/0120564 A1 | 5/2016 | Kirkpatrick et al. |
| 2016/0128770 A1 | 5/2016 | Afonso et al. |
| 2016/0166167 A1 | 6/2016 | Narayan et al. |
| 2016/0166310 A1 | 6/2016 | Stewart et al. |
| 2016/0166311 A1 | 6/2016 | Long et al. |
| 2016/0174865 A1 | 6/2016 | Stewart et al. |
| 2016/0183877 A1 | 6/2016 | Williams et al. |
| 2016/0184003 A1 | 6/2016 | Srimathveeravalli et al. |
| 2016/0184004 A1 | 6/2016 | Hull et al. |
| 2016/0213282 A1 | 7/2016 | Leo et al. |
| 2016/0220307 A1 | 8/2016 | Miller et al. |
| 2016/0235470 A1 | 8/2016 | Callas et al. |
| 2016/0249972 A1* | 9/2016 | Klink ............... A61B 18/14 606/48 |
| 2016/0256682 A1 | 9/2016 | Paul et al. |
| 2016/0287314 A1 | 10/2016 | Arena et al. |
| 2016/0310211 A1 | 10/2016 | Long |
| 2016/0324564 A1 | 11/2016 | Gerlach et al. |
| 2016/0324573 A1 | 11/2016 | Mickelson et al. |
| 2016/0331441 A1 | 11/2016 | Konings |
| 2016/0331459 A1 | 11/2016 | Townley et al. |
| 2016/0338770 A1 | 11/2016 | Bar-Tal et al. |
| 2016/0354142 A1 | 12/2016 | Pearson et al. |
| 2016/0361109 A1 | 12/2016 | Weaver et al. |
| 2017/0001016 A1 | 1/2017 | De Ridder |
| 2017/0035499 A1 | 2/2017 | Stewart et al. |
| 2017/0042449 A1 | 2/2017 | Deno et al. |
| 2017/0042615 A1 | 2/2017 | Salahieh et al. |
| 2017/0056648 A1 | 3/2017 | Syed et al. |
| 2017/0065330 A1 | 3/2017 | Mickelsen et al. |
| 2017/0065339 A1 | 3/2017 | Mickelsen |
| 2017/0065340 A1 | 3/2017 | Long |
| 2017/0065343 A1 | 3/2017 | Mickelsen |
| 2017/0071543 A1 | 3/2017 | Basu et al. |
| 2017/0095291 A1 | 4/2017 | Harrington et al. |
| 2017/0105793 A1 | 4/2017 | Cao et al. |
| 2017/0146584 A1 | 5/2017 | Daw et al. |
| 2017/0151014 A1 | 6/2017 | Perfler |
| 2017/0151029 A1 | 6/2017 | Mickelsen |
| 2017/0164999 A1 | 6/2017 | Hettel |
| 2017/0172654 A1 | 6/2017 | Wittkampf et al. |
| 2017/0181795 A1 | 6/2017 | Debruyne |
| 2017/0189097 A1 | 7/2017 | Viswanathan et al. |
| 2017/0215953 A1 | 8/2017 | Long et al. |
| 2017/0245928 A1 | 8/2017 | Xiao et al. |
| 2017/0246455 A1 | 8/2017 | Athos et al. |
| 2017/0312024 A1 | 11/2017 | Harlev et al. |
| 2017/0312025 A1 | 11/2017 | Harlev et al. |
| 2017/0312027 A1 | 11/2017 | Harlev et al. |
| 2018/0001056 A1 | 1/2018 | Leeflang et al. |
| 2018/0028252 A1 | 2/2018 | Lalonde |
| 2018/0042674 A1 | 2/2018 | Mickelsen |
| 2018/0042675 A1 | 2/2018 | Long |
| 2018/0043153 A1 | 2/2018 | Viswanathan et al. |
| 2018/0064488 A1 | 3/2018 | Long et al. |
| 2018/0085160 A1 | 3/2018 | Viswanathan et al. |
| 2018/0093088 A1 | 4/2018 | Mickelsen |
| 2018/0133460 A1 | 5/2018 | Townley et al. |
| 2018/0161093 A1 | 6/2018 | Basu et al. |
| 2018/0168511 A1 | 6/2018 | Hall et al. |
| 2018/0184982 A1 | 7/2018 | Basu et al. |
| 2018/0193090 A1 | 7/2018 | De et al. |
| 2018/0200497 A1 | 7/2018 | Mickelsen |
| 2018/0235496 A1 | 8/2018 | Wu et al. |
| 2018/0256109 A1 | 9/2018 | Wu et al. |
| 2018/0280080 A1 | 10/2018 | Govari et al. |
| 2018/0303488 A1 | 10/2018 | Hill |
| 2018/0303543 A1 | 10/2018 | Stewart et al. |
| 2018/0311497 A1 | 11/2018 | Viswanathan et al. |
| 2018/0344202 A1 | 12/2018 | Bar-Tal et al. |
| 2018/0344393 A1 | 12/2018 | Gruba et al. |
| 2018/0360531 A1 | 12/2018 | Holmes et al. |
| 2018/0360534 A1 | 12/2018 | Teplitsky et al. |
| 2019/0015007 A1 | 1/2019 | Rottmann et al. |
| 2019/0015638 A1 | 1/2019 | Gruba et al. |
| 2019/0030328 A1 | 1/2019 | Stewart et al. |
| 2019/0046791 A1 | 2/2019 | Ebbers et al. |
| 2019/0069950 A1 | 3/2019 | Viswanathan et al. |
| 2019/0076179 A1 | 3/2019 | Babkin et al. |
| 2019/0125788 A1 | 5/2019 | Gruba et al. |
| 2019/0143106 A1 | 5/2019 | Dewitt et al. |
| 2019/0151015 A1 | 5/2019 | Viswanathan et al. |
| 2019/0175263 A1 | 6/2019 | Altmann et al. |
| 2019/0183378 A1 | 6/2019 | Mosesov et al. |
| 2019/0183567 A1 | 6/2019 | Govari et al. |
| 2019/0192223 A1 | 6/2019 | Rankin |
| 2019/0201089 A1 | 7/2019 | Waldstreicher et al. |
| 2019/0201688 A1 | 7/2019 | Olson |
| 2019/0209235 A1 | 7/2019 | Stewart et al. |
| 2019/0223948 A1 | 7/2019 | Stewart et al. |
| 2019/0231421 A1 | 8/2019 | Viswanathan et al. |
| 2019/0231425 A1 | 8/2019 | Waldstreicher et al. |
| 2019/0254735 A1 | 8/2019 | Stewart et al. |
| 2019/0269912 A1 | 9/2019 | Viswanathan et al. |
| 2019/0298442 A1 | 10/2019 | Ogata et al. |
| 2019/0307500 A1 | 10/2019 | Byrd et al. |
| 2019/0350647 A1 | 11/2019 | Ramberg et al. |
| 2019/0350649 A1 | 11/2019 | Sutermeister et al. |
| 2020/0008869 A1 | 1/2020 | Byrd |
| 2020/0008870 A1 | 1/2020 | Gruba et al. |
| 2020/0009378 A1 | 1/2020 | Stewart et al. |
| 2020/0038104 A1 | 2/2020 | Mickelsen |
| 2020/0046423 A1 | 2/2020 | Viswanathan et al. |
| 2020/0085484 A1 | 3/2020 | Tegg et al. |

FOREIGN PATENT DOCUMENTS

| | | |
|---|---|---|
| EP | 0797956 B1 | 6/2003 |
| EP | 1340469 A1 | 9/2003 |
| EP | 1127552 B1 | 6/2006 |
| EP | 1803411 A2 | 7/2007 |
| EP | 1009303 B1 | 6/2009 |
| EP | 2213729 A2 | 8/2010 |
| EP | 2382935 A1 | 11/2011 |
| EP | 2425871 A2 | 3/2012 |
| EP | 2532320 A2 | 12/2012 |
| EP | 2587275 A1 | 5/2013 |
| EP | 2663227 A1 | 11/2013 |
| EP | 1909678 B1 | 1/2014 |
| EP | 2217165 B1 | 3/2014 |
| EP | 2376193 B1 | 3/2014 |
| EP | 2708181 A1 | 3/2014 |
| EP | 2777579 A1 | 9/2014 |
| EP | 2777585 A1 | 9/2014 |
| EP | 2934307 A1 | 10/2015 |
| EP | 3056242 A1 | 8/2016 |
| EP | 3111871 A1 | 1/2017 |
| EP | 3151773 B1 | 4/2018 |
| JP | 06-507797 A | 9/1994 |
| JP | 10-137207 A | 5/1998 |
| JP | 2000-508196 A | 7/2000 |
| JP | 2000-513625 A | 10/2000 |
| JP | 2005-516666 A | 6/2005 |
| JP | 2006-506184 A | 2/2006 |
| JP | 2008-538997 A | 11/2008 |
| JP | 2009-500052 A | 1/2009 |
| JP | 2009-500129 A | 1/2009 |
| JP | 2011-509158 A | 3/2011 |
| JP | 2012-050538 A | 3/2012 |
| JP | 2017-104547 A | 6/2017 |
| JP | 2018-108376 A | 7/2018 |
| JP | 2020-503097 A | 1/2020 |
| WO | 92/07622 A1 | 5/1992 |
| WO | 92/21278 A1 | 12/1992 |
| WO | 92/21285 A1 | 12/1992 |
| WO | 94/07413 A1 | 4/1994 |
| WO | 97/24073 A1 | 7/1997 |

(56) References Cited

FOREIGN PATENT DOCUMENTS

| | | |
|---|---|---|
| WO | 97/25917 A1 | 7/1997 |
| WO | 97/37719 A1 | 10/1997 |
| WO | 99/04851 A1 | 2/1999 |
| WO | 99/22659 A1 | 5/1999 |
| WO | 99/56650 A1 | 11/1999 |
| WO | 99/59486 A2 | 11/1999 |
| WO | 02/56782 A2 | 7/2002 |
| WO | 03/53289 A1 | 7/2003 |
| WO | 03/65916 A1 | 8/2003 |
| WO | 2004/045442 A1 | 6/2004 |
| WO | 2004/086994 A1 | 10/2004 |
| WO | 2005/046487 A1 | 5/2005 |
| WO | 2006/115902 A2 | 11/2006 |
| WO | 2007/006055 A2 | 1/2007 |
| WO | 2007/079438 A2 | 7/2007 |
| WO | 2009/082710 A1 | 7/2009 |
| WO | 2009/089343 A1 | 7/2009 |
| WO | 2009/137800 A2 | 11/2009 |
| WO | 2010/014480 A1 | 2/2010 |
| WO | 2011/028310 A1 | 3/2011 |
| WO | 2011/154805 A1 | 12/2011 |
| WO | 2012/051433 A2 | 4/2012 |
| WO | 2012/097067 A1 | 7/2012 |
| WO | 2012/153928 A2 | 11/2012 |
| WO | 2013/019385 A1 | 2/2013 |
| WO | 2014/025394 A1 | 2/2014 |
| WO | 2014/031800 A1 | 2/2014 |
| WO | 2014/036439 A2 | 3/2014 |
| WO | 2014/100579 A1 | 6/2014 |
| WO | 2014/160832 A2 | 10/2014 |
| WO | 2015/049784 A1 | 4/2015 |
| WO | 2015/066322 A1 | 5/2015 |
| WO | 2015/099786 A1 | 7/2015 |
| WO | 2015/103530 A1 | 7/2015 |
| WO | 2015/103574 A1 | 7/2015 |
| WO | 2015/130824 A1 | 9/2015 |
| WO | 2015/140741 A1 | 9/2015 |
| WO | 2015/143327 A1 | 9/2015 |
| WO | 2015/171921 A2 | 11/2015 |
| WO | 2015/175944 A1 | 11/2015 |
| WO | 2015/192018 A1 | 12/2015 |
| WO | 2015/192027 A1 | 12/2015 |
| WO | 2016/059027 A1 | 4/2016 |
| WO | 2016/060983 A1 | 4/2016 |
| WO | 2016/081650 A1 | 5/2016 |
| WO | 2016/090175 A1 | 6/2016 |
| WO | 2017/093926 A1 | 6/2017 |
| WO | 2017/119934 A1 | 7/2017 |
| WO | 2017/120169 A1 | 7/2017 |
| WO | 2017/192477 A1 | 11/2017 |
| WO | 2017/192495 A1 | 11/2017 |
| WO | 2017/201504 A1 | 11/2017 |
| WO | 2017/218734 A1 | 12/2017 |
| WO | 2018/005511 A1 | 1/2018 |
| WO | 2018/106569 A1 | 6/2018 |
| WO | 2018/106688 A2 | 6/2018 |
| WO | 2018/200800 A1 | 11/2018 |
| WO | 2019/023259 A2 | 1/2019 |
| WO | 2019/023280 A1 | 1/2019 |
| WO | 2019/035071 A1 | 2/2019 |
| WO | 2019/133606 A1 | 7/2019 |
| WO | 2019/133608 A1 | 7/2019 |
| WO | 2019/136218 A1 | 7/2019 |
| WO | 2019/181612 A1 | 9/2019 |
| WO | 2019/234133 A1 | 12/2019 |

OTHER PUBLICATIONS

Hobbs, E. P., "Investor Relations Update: Tissue Ablation via Irreversible Electroporation (IRE)," Powerpoint (2004), 16 pages.
International Search Report and Written Opinion for International Application No. PCT/US2019/051998, dated Feb. 26, 2020, 11 pages.
Lavee, J. et al., "A Novel Nonthermal Energy Source for Surgical Epicardial Atrial Ablation: Irreversible Electroporation," The Heart Surgery Forum #2006-1202, 10(2), 2007 [Epub Mar. 2007].
Madhavan, M. et al., "Novel Percutaneous Epicardial Autonomic Modulation in the Canine for Atrial Fibrillation: Results of an Efficacy and Safety Study," Pace, 00:1-11 (2016).
Neven, K. et al., "Epicardial linear electroporation ablation and lesion size," Heart Rhythm, 11:1465-1470 (2014).
Neven, K. et al., "Myocardial Lesion Size After Epicardial Electroporation Catheter Ablation After Subxiphoid Puncture," Circ Arrhythm Electrophysiol., 7(4):728-733 (2014).
Neven, K. et al., "Safety and Feasibility of Closed Chest Epicardial Catheter Ablation Using Electroporation," Circ Arrhythm Electrophysiol., 7:913-919 (2014).
Van Driel, V.J.H.M. et al., "Low vulnerability of the right phrenic nerve to electroporation ablation," Heart Rhythm, 12:1838-1844 (2015).
Van Driel, V.J.H.M. et al., "Pulmonary Vein Stenosis After Catheter Ablation Electroporation Versus Radiofrequency," Circ Arrhythm Electrophysiol., 7(4):734-738 (2014).
Wittkampf, F.H. et al., "Feasibility of Electroporation for the Creation of Pulmonary Vein Ostial Lesions," J Cardiovasc Electrophysiol, 22(3):302-309 (Mar. 2011).
Wittkampf, F.H. et al., "Myocardial Lesion Depth With Circular Electroporation Ablation," Circ. Arrhythm Electrophysiol., 5(3):581-586 (2012).
Office Action received for Japanese Patent Application No. 2021-515144, mailed on Jul. 4, 2023, 14 pages (7 pages of English Translation and 7 pages of Original Document).
Office Action received for Japanese Patent Application No. 2021-515144, mailed on Mar. 19, 2024, 4 pages (2 pages of English Translation and 2 pages of Original Document).

* cited by examiner

SYSTEMS, APPARATUSES, AND METHODS FOR DELIVERY OF PULSED ELECTRIC FIELD ABLATIVE ENERGY TO ENDOCARDIAL TISSUE

CROSS-REFERENCE TO RELATED APPLICATIONS

This application is a continuation of International Patent Application No. PCT/US2019/051998, filed on Sep. 19, 2019, which claims the benefit of U.S. Provisional Application No. 62/734,214, filed on Sep. 20, 2018, the entire disclosures of which are incorporated herein by reference in their entirety.

BACKGROUND

The generation of pulsed electric fields for tissue therapeutics has moved from the laboratory to clinical applications over the past two decades, while the effects of brief pulses of high voltages and large electric fields on tissue have been investigated for the past forty years or more. Application of brief high DC voltages to tissue may generate locally high electric fields typically in the range of hundreds of volts per centimeter that disrupt cell membranes by generating pores in the cell membrane. While the precise mechanism of this electrically-driven pore generation or electroporation continues to be studied, it is thought that the application of relatively brief and large electric fields generates instabilities in the lipid bilayers in cell membranes, causing the occurrence of a distribution of local gaps or pores in the cell membrane. This electroporation may be irreversible if the applied electric field at the membrane is larger than a threshold value such that the pores do not close and remain open, thereby permitting exchange of biomolecular material across the membrane leading to necrosis and/or apoptosis (cell death). Subsequently, the surrounding tissue may heal naturally.

While pulsed DC voltages may drive electroporation under the right circumstances, there remains an unmet need for thin, flexible, atraumatic devices that effectively deliver high DC voltage electroporation ablation therapy selectively to endocardial tissue in regions of interest while minimizing damage to healthy tissue.

BRIEF SUMMARY

Described here are systems, devices, and methods for ablating tissue through irreversible electroporation. In some embodiments, an apparatus can include a first shaft having a longitudinal axis and defining a lumen; a second shaft disposed within the lumen and having a distal portion that extends from a distal portion of the first shaft, the second shaft moveable along the longitudinal axis relative to the first shaft; a first electrode coupled to the distal portion of the first shaft; a second electrode coupled to the distal portion of the second shaft, the first and second electrodes configured to generate an electric field for ablating tissue; and an inflatable member disposed between the first and second electrodes, the inflatable member configured to transition from an undeployed configuration to a deployed configuration in response to the second shaft being moved proximally relative to the first shaft, the inflatable member in the deployed configuration configured to engage a wall of a pulmonary vein ostium and direct the electric field generated by the first and second electrodes toward the wall.

In some embodiments, an apparatus can include a shaft having a longitudinal axis and defining a lumen; an inflatable member disposed near a distal portion of the shaft, the inflatable member configured to transition between an undeployed configuration and a deployed configuration, the inflatable member including a wall having a proximal portion, a distal portion, and a middle portion disposed between the proximal and distal portions of the wall, the middle portion having a minimum thickness that is less than a thickness of the proximal and distal portions of the wall; and first and second electrodes disposed on opposite sides of the inflatable member along the longitudinal axis, the first and second electrodes configured to generate an electric field for ablating tissue.

In some embodiments, a system can include a signal generator configured to generate a pulse waveform; an ablation device coupled to the signal generator, the ablation device including: first and second electrodes configured to receive the pulse waveform and generate an electric field for ablation; and an inflatable member formed of an insulating material and disposed between the first and second electrodes, the inflatable member configured to transition between an undeployed configuration in which the inflatable member can be advanced to a pulmonary vein ostium to a deployed configuration in which the inflatable member can engage with a wall of the pulmonary vein ostium, the inflatable member in the deployed configuration configured to direct the electric field toward the wall.

In some embodiments, a method can include retracting an inner shaft of an ablation device relative to an outer shaft of the ablation device, the inner shaft disposed within a lumen of the outer shaft; transitioning, in response to retracting the inner shaft relative to the outer shaft, an inflatable member of the ablation device from an undeployed configuration to a deployed configuration in which a side portion of the inflatable member engages a wall of a pulmonary vein ostium; and delivering, after the transitioning, a pulse waveform to first and second electrodes of the ablation device such that the first and second electrodes generate an electric field for ablating the wall of the pulmonary vein ostium, the first and second electrodes disposed on opposite sides of the inflatable member.

DETAILED DESCRIPTION

Figure 1:
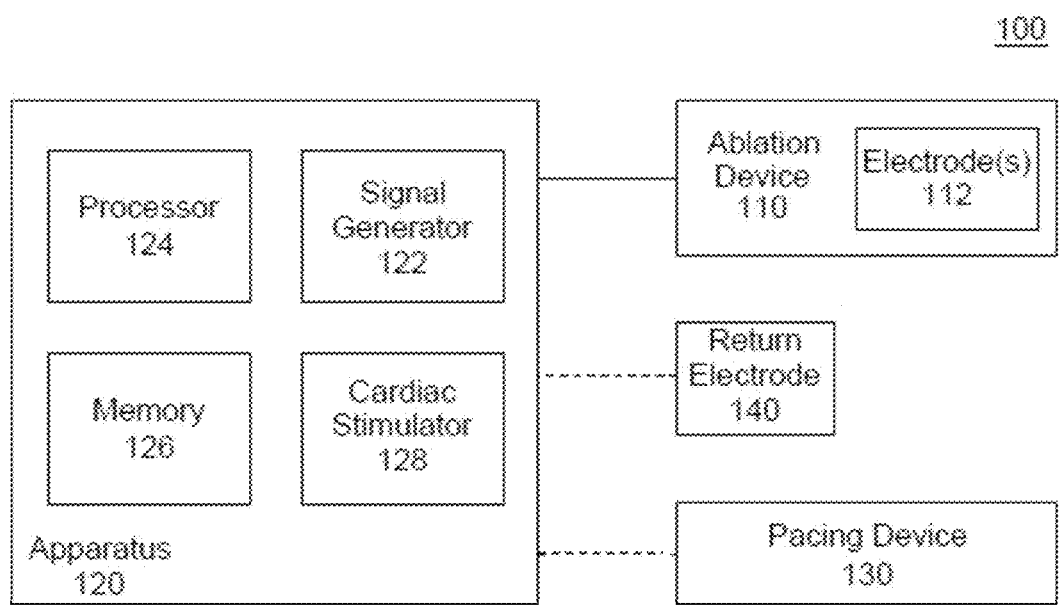
FIG. 1 is a block diagram of an electroporation system, according to embodiments.

Described here are systems, devices, and methods for ablating tissue through irreversible electroporation. Generally, an apparatus for delivering a pulse waveform to tissue may include a first catheter (e.g., shaft) defining a longitudinal axis. An expandable/inflatable member may be coupled to a distal portion of the first catheter. A first electrode may be coupled to the distal portion of the first catheter and proximal to the inflatable member. A second catheter (e.g., shaft) or tubular lumen may be disposed within a lumen of the first catheter and a chamber of the expandable/inflatable member where the second catheter may be slidable relative to the first catheter. The expandable/inflatable member may be coupled to a distal end of the second catheter. A second electrode may be coupled to the distal portion of the second catheter and distal to the inflatable member. In some embodiments the second catheter, and in particular its distal portion, may be steerable linearly relative to the first catheter. Thus in some embodiments, the second electrode may be steerable relative to the first electrode. A proximal portion of the expandable/inflatable member may be coupled to the distal portion of the first catheter and a distal portion of the expandable/inflatable member may be coupled to the distal portion of the second catheter or tubular lumen. The second catheter may have a lumen diameter sufficient to pass a guidewire through the lumen. The guidewire may provide mechanical support for the first and second catheters. In some embodiments, the first electrode may comprise a first set of electrodes and the second electrode may comprise a second set of electrodes.

Generally, a system for delivering a pulse waveform to tissue may include a signal generator configured for generating a pulse waveform and an ablation device coupled to the signal generator and configured to receive the pulse waveform. The ablation device may include an expandable/inflatable member (e.g., a balloon) coupled to a distal portion of a first catheter for delivering energy to ablate tissue by irreversible electroporation. One or more electrodes may be formed proximal to the expandable/inflatable member on a surface of the first catheter.

In some embodiments, a system may include a signal generator configured for generating a pulse waveform. An ablation device may be coupled to the signal generator and configured for receiving the pulse waveform. The ablation device may include a handle configured to move the second electrode relative to the first electrode. The system may include a cardiac stimulator for generation of pacing signals and for delivery of pulse waveforms in synchrony with the pacing signal. In some embodiments, one or more of the electrodes may have an insulated electrical lead associated therewith, the insulated electrical lead configured for sustaining a voltage potential of at least about 700 V without dielectric breakdown of its corresponding insulation, the insulated electrical lead disposed in a lumen of the catheter. In some embodiments, one or more of the electrodes may be independently addressable.

In some embodiments, a pulse waveform may include a first level of a hierarchy of the pulse waveform in the form of a first set of pulses, each pulse having a pulse time duration, a first time interval separating successive pulses. A second level of the hierarchy of the pulse waveform includes a plurality of first sets of pulses as a second set of pulses, a second time interval separating successive first sets of pulses, the second time interval being at least three times the duration of the first time interval. A third level of the hierarchy of the pulse waveform includes a plurality of second sets of pulses as a third set of pulses, a third time interval separating successive second sets of pulses, the third time interval being at least thirty times the duration of the second level time interval. In some of these embodiments, the pulse waveform includes a fourth level of the hierarchy of the pulse waveform includes a plurality of third sets of pulses as a fourth set of pulses, a fourth time interval separating successive third sets of pulses, the fourth time interval being at least ten times the duration of the third level time interval.

In some embodiments, a distal portion of the ablation device may further include a radiopaque portion. In some embodiments, the second catheter defines a lumen therethrough.

In some embodiments, a method of ablation via irreversible electroporation includes the steps of advancing an ablation device towards a pulmonary vein ostium. The ablation device may include a first catheter, a second catheter or tubular lumen, and an expandable/inflatable member coupled to a distal end of the catheter shaft. The inflatable member may be flanked by electrodes mounted on the device proximal and distal to the inflatable member. A pulse waveform may be generated. The pulse waveform may be delivered to the pulmonary vein ostium via the electrodes on the ablation device.

In some embodiments, the expandable/inflatable member of the ablation device may be transitioned from a first configuration to a second configuration. In some embodiments, transitioning the expandable/inflatable member from the first configuration to the second configuration includes infusing the expandable/inflatable member with distilled or deionized water which may induce mechanically expansion. In some embodiments, pulsed electric field ablation energy may be delivered through the first set of electrodes and the second set of electrodes of the ablation device. In some embodiments, the ablation device is configured to generate an electric field intensity of between about 200 V/cm and about 800 V/cm.

In some embodiments, the ablation device may include a handle. In some embodiments, a portion of the first catheter shaft proximal to the proximal or first set of electrodes can be deflectable, with the deflection controlled by a knob or other control mechanism on the handle. The method may further include the steps of deflecting a portion of the ablation device using the handle. For example, a second electrode may be moved relative to the first electrode and the shape of the expandable/inflatable member in the second configuration may be modified by infusion of distilled or deionized water through an infusion port attached to the handle, and the distal shaft may be deflected using a deflection knob on the handle.

In some embodiments, the method may include the steps of creating a transseptal opening into a left atrium, advancing a guidewire and a steerable sheath into the left atrium through the transseptal opening, and advancing the ablation device into a pulmonary vein over the guidewire. In some embodiments, the method may include the steps of creating a first access site in a patient, advancing the guidewire through the first access site and into a right atrium, advancing the dilator and a steerable sheath over the guidewire and into the right atrium, advancing the dilator from the right atrium into the left atrium through an interatrial septum to create the transseptal opening, and dilating the transseptal opening using the dilator. In some embodiments, a second access site may be created in the patient for advancing a cardiac pacing catheter. In some embodiments, the method may include the steps of advancing the pacing catheter into a right ventricle, generating a pacing signal for cardiac stimulation of the heart using the cardiac stimulator, and applying the pacing signal to the heart using the cardiac stimulator, and then delivering a pulsed electric field voltage pulse waveform in synchronization with the pacing signal once the ablation device with the inflatable member is suitably positioned at a pulmonary vein ostium.

In some embodiments, the method may include the step of fluoroscopically imaging a radiopaque portion of the ablation device during one or more steps. In some embodiments, the first access site is a femoral vein. In some embodiments, the interatrial septum includes a fossa ovalis.

In some embodiments, the pulse waveform may include a first level of a hierarchy of the pulse waveform in the form of a first set of pulses, each pulse having a pulse time duration, a first time interval separating successive pulses. A second level of the hierarchy of the pulse waveform includes a plurality of first sets of pulses as a second set of pulses, a second time interval separating successive first sets of pulses, the second time interval being at least three times the duration of the first time interval. A third level of the hierarchy of the pulse waveform includes a plurality of second sets of pulses as a third set of pulses, a third time interval separating successive second sets of pulses, the third time interval being at least thirty times the duration of the second level time interval. In some of these embodiments, the pulse waveform includes a fourth level of the hierarchy of the pulse waveform includes a plurality of third sets of pulses as a fourth set of pulses, a fourth time interval separating successive third sets of pulses, the fourth time interval being at least ten times the duration of the third level time interval.

The systems, devices, and methods described herein may be used to generate large electric field magnitudes at desired regions of interest to generate irreversible electroporation. An irreversible electroporation system as described herein may include a signal generator and a processor configured to apply one or more voltage pulse waveforms to a set of electrodes to deliver energy to a region of interest. The pulse waveforms disclosed herein may aid in therapeutic treatment of cardiac arrhythmias such as atrial fibrillation. In order to deliver the pulse waveforms generated by the signal generator, one or more electrodes of the ablation device may have an insulated electrical lead configured for sustaining a voltage potential of at least about 700 V without dielectric breakdown of its corresponding insulation. In some embodiments, at least some of the electrodes may be independently addressable such that each electrode may be controlled (e.g., deliver energy) independently of any other electrode of the device.

The term "electroporation" as used herein refers to the application of an electric field to a cell membrane to change the permeability of the cell membrane to the extracellular environment. The term "reversible electroporation" as used herein refers to the application of an electric field to a cell membrane to temporarily change the permeability of the cell membrane to the extracellular environment. For example, a cell undergoing reversible electroporation can observe the temporary and/or intermittent formation of one or more pores in its cell membrane that close up upon removal of the electric field. The term "irreversible electroporation" as used herein refers to the application of an electric field to a cell membrane to permanently change the permeability of the cell membrane to the extracellular environment. For example, a cell undergoing irreversible electroporation can observe the formation of one or more pores in its cell membrane that persist upon removal of the electric field.

Pulse waveforms for electroporation energy delivery as disclosed herein may enhance the safety, efficiency and effectiveness of energy delivery to tissue by reducing the electric field threshold associated with irreversible electroporation, thus yielding more effective ablative lesions with a reduction in total energy delivered. In some embodiments, the voltage pulse waveforms disclosed herein may be hierarchical and have a nested structure. For example, the pulse waveform may include hierarchical groupings of pulses having associated timescales. In some embodiments, the methods, systems, and devices disclosed herein may comprise one or more of the methods, systems, and devices described in one or more of International Application Serial No. PCT/US2016/057664, filed on Oct. 19, 2016, and titled "SYSTEMS, APPARATUSES AND METHODS FOR DELIVERY OF ABLATIVE ENERGY TO TISSUE," and U.S. patent application Ser. No. 16/405,515, filed on May 7, 2019, and titled "SYSTEMS, APPARATUSES AND METHODS FOR DELIVERY OF ABLATIVE ENERGY TO TISSUE," the contents of each of which are hereby incorporated by reference in its entirety.

In some embodiments, the systems may further include a cardiac stimulator used to synchronize the generation of the pulse waveform to a paced heartbeat. The cardiac stimulator may electrically pace the heart with a cardiac stimulator and ensure pacing capture to establish periodicity and predictability of the cardiac cycle. A time window within a refractory period of the periodic cardiac cycle may be selected for voltage pulse waveform delivery. Thus, voltage pulse waveforms may be delivered in the refractory period of the cardiac cycle so as to avoid disruption of the sinus rhythm of the heart. In some embodiments, an ablation device may include one or more catheters, guidewires, expandable/inflatable members, and electrodes. The ablation device may transform into different configurations (e.g., deflated and inflated) to position the device within an endocardial space.

Generally, to ablate tissue, one or more catheters may be advanced in a minimally invasive fashion through vasculature to a target location. The methods described here may include introducing a device into an endocardial space of the heart and disposing the device at the ostium of a pulmonary vein. A pulse waveform may be generated and delivered to electrodes of the device to ablate tissue. In some embodiments, the pulse waveform may be generated in synchronization with a pacing signal of the heart to avoid disruption of the sinus rhythm of the heart. In some embodiments, the electrodes may be configured in anode-cathode subsets. The pulse waveform may include hierarchical waveforms to aid in tissue ablation and reduce damage to healthy tissue.

I. Systems

Overview

Disclosed herein are systems and devices configured for tissue ablation via the selective and rapid application of voltage pulse waveforms to aid tissue ablation, resulting in irreversible electroporation. Generally, a system for ablating tissue described here may include a signal generator and an ablation device having one or more electrodes and an expandable/inflatable member (e.g., balloon) for the selective and rapid application of DC voltage to drive electroporation. As described herein, the systems and devices may be deployed endocardially to treat cardiac arrhythmias. Voltage pulse waveforms may be applied to a subset of the electrodes, with suitable anode/cathode electrode selections. A pacing signal for cardiac stimulation may be generated and used to generate the pulse waveform by the signal generator in synchronization with the pacing signal.

Generally, the systems and devices described herein include one or more catheters configured to ablate tissue in a ventricle of a heart. FIG. 1 illustrates an ablation system (100) configured to deliver voltage pulse waveforms. The system (100) may include an apparatus (120) including a signal generator (122), processor (124), memory (126), and cardiac stimulator (128). The apparatus (120) may be coupled to an ablation device (110), and optionally to a pacing device (130).

The signal generator (122) may be configured to generate pulse waveforms for irreversible electroporation of tissue, such as, for example, a pulmonary vein. For example, the signal generator (122) may be a voltage pulse waveform generator and be configured to deliver a pulse waveform to the ablation device (110). The return electrode (140) in some embodiments may be coupled to a patient (e.g., disposed on a patient's back) to allow current to pass from the ablation device (110) through the patient and then to the return electrode (140). In other embodiments, an electrode of the ablation device may serve as a return, such that a separate return electrode (140) may be absent. The processor (124) may incorporate data received from memory (126) to determine the parameters of the pulse waveform to be generated by the signal generator (122), while some parameters such as voltage can be input by a user. The memory (126) may further store instructions to cause the signal generator (122) to execute modules, processes and/or functions associated with the system (100), such as pulse waveform generation and/or cardiac pacing synchronization. For example, the memory (126) may be configured to store pulse waveform and/or heart pacing data for pulse waveform generation and/or cardiac pacing, respectively.

In some embodiments, the ablation device (110) may include a catheter having an expandable/inflatable member (e.g., balloon) configured to deliver the pulse waveforms described in more detail below. In each of the embodiments described herein, the expandable/inflatable member may be inflated using, for example, saline or, in some cases, an electrically non-conducting or very poorly conducting fluid (e.g., gas, liquid such as distilled water, deionized water, etc.). Fluid may be input through a lumen of a catheter coupled to the expandable/inflatable member. For example, the ablation device (110) may be introduced into an endocardial space and positioned at the ostium of a pulmonary vein and inflated so that the inflatable member is well apposed or engaged at the walls of the pulmonary vein, and then the pulse waveforms may be delivered to ablate tissue. The ablation device (110) may include one or more electrodes (112), which may, in some embodiments, be independently addressable electrodes. Each electrode may include an insulated electrical lead configured to sustain a voltage potential of at least about 700 V without dielectric breakdown of its corresponding insulation. In some embodiments, the insulation on each of the electrical leads may sustain an electrical potential difference of between about 200 V to about 3,000 V across its thickness without dielectric breakdown. For example, the electrodes (112) may be grouped into one or more anode-cathode subsets such as, for example, a subset including one proximal electrode and one distal electrode. In some embodiments, the distal electrode may include at least a portion of an expandable/inflatable member. As used herein, proximal is towards a handle of an ablation device and distal is towards a tip end of the ablation device.

When used, the pacing device (130) may be suitably coupled to the patient (not shown) and configured to receive a heart pacing signal generated by the cardiac stimulator (128). An indication of the pacing signal may be transmitted by the cardiac stimulator (128) to the signal generator (122). Based on detection of the pacing signal by the generator, a voltage pulse waveform may be generated by the signal generator (122) for ablation delivery. In some embodiments, the signal generator (122) may be configured to generate the pulse waveform in synchronization with the indication of the pacing signal (e.g., such that the ablation delivery occurs during a refractory window of a cardiac chamber). In some embodiments, the refractory window may be a common refractory window of two cardiac chambers such as an atrium and a ventricle. For example, in some embodiments, the common refractory window may start substantially immediately following a ventricular pacing signal (or after a very small delay) and last for a duration of approximately 250 ms or less thereafter. In such embodiments, an entire pulse waveform may be delivered within this duration.

The processor (124) may be any suitable processing device configured to run and/or execute a set of instructions or code. The processor may be, for example, a general purpose processor, a Field Programmable Gate Array (FPGA), an Application Specific Integrated Circuit (ASIC), a Digital Signal Processor (DSP), and/or the like. The processor may be configured to run and/or execute application processes and/or other modules, processes and/or functions associated with the system and/or a network associated therewith (not shown). The underlying device technologies may be provided in a variety of component types, e.g., metal-oxide semiconductor field-effect transistor (MOSFET) technologies like complementary metal-oxide semiconductor (CMOS), bipolar technologies like emitter-coupled logic (ECL), polymer technologies (e.g., silicon-conjugated polymer and metal-conjugated polymer-metal structures), mixed analog and digital, and/or the like.

The memory (126) may include a database (not shown) and may be, for example, a random access memory (RAM), a memory buffer, a hard drive, an erasable programmable read-only memory (EPROM), an electrically erasable read-only memory (EEPROM), a read-only memory (ROM), Flash memory, etc. The memory (126) may store instructions to cause the processor (124) to execute modules, processes and/or functions associated with the system (100), such as pulse waveform generation and/or cardiac pacing.

The system (100) may be in communication with other devices (not shown) via, for example, one or more networks, each of which may be any type of network. A wireless network may refer to any type of digital network that is not connected by cables of any kind. However, a wireless network may connect to a wireline network in order to interface with the Internet, other carrier voice and data networks, business networks, and personal networks. A wireline network is typically carried over copper twisted pair, coaxial cable or fiber optic cables. There are many different types of wireline networks including, wide area networks (WAN), metropolitan area networks (MAN), local area networks (LAN), campus area networks (CAN), global area networks (GAN), like the Internet, and virtual private networks (VPN). Hereinafter, network refers to any combination of combined wireless, wireline, public and private data networks that are typically interconnected through the Internet, to provide a unified networking and information access solution.

Ablation Device

Figure 2A:
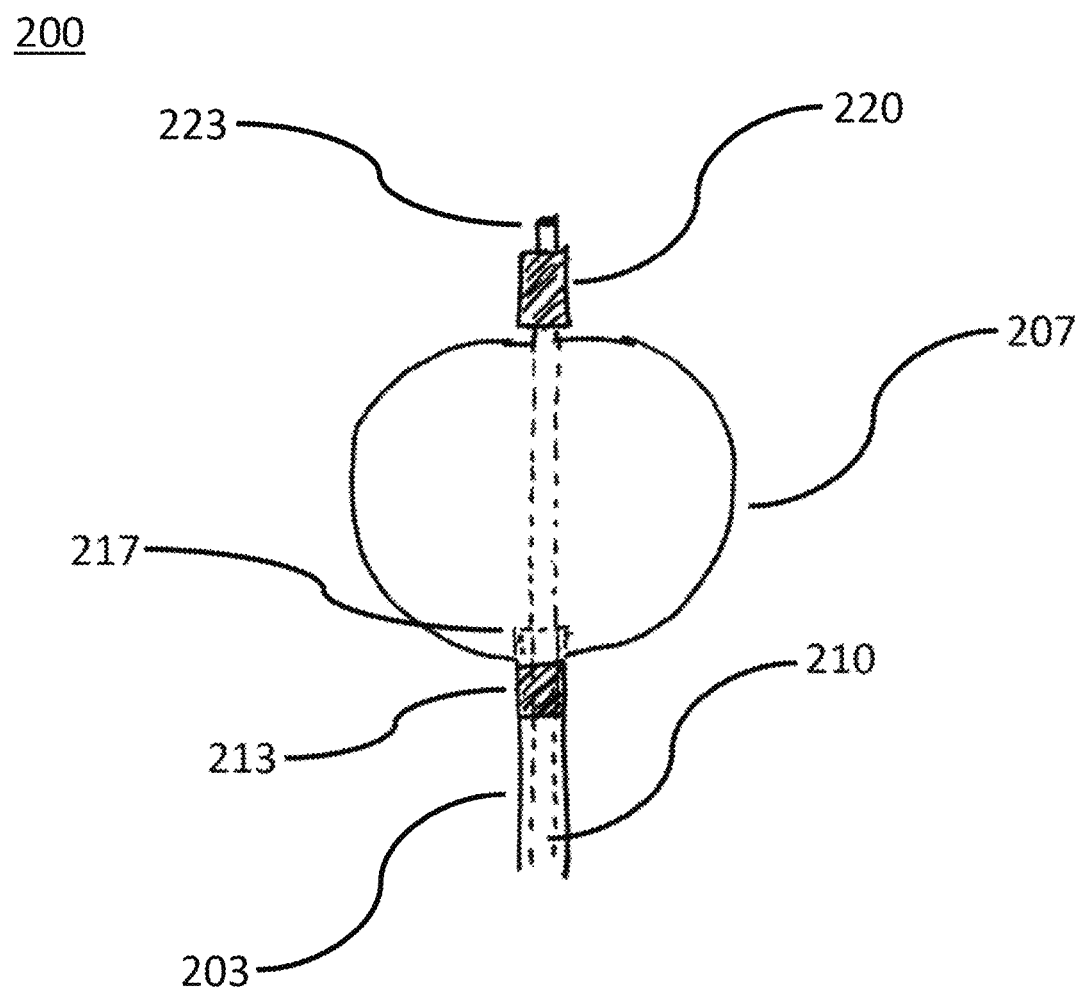
FIG. 2A is a side view of an ablation device in an inflated state, according to embodiments.

The systems described here may include one or more multi-electrode ablation devices configured to ablate tissue in a pulmonary vein of a heart for treating indications such as arrhythmia. FIG. 2A is a side view of an ablation device (200) (e.g., structurally and/or functionally similar to the ablation device (110)) including a first catheter (203) (e.g., catheter shaft or outer shaft) defining a lumen, a second catheter (210) (e.g., a tubular guidewire or inner shaft defining a lumen), and an inflatable member (207). The second catheter (210) may be disposed within a lumen of the first catheter (203) and a chamber of the inflatable member (207) where the second catheter (210) may be slidable relative to the first catheter (203). The inflatable member (e.g., balloon) (207) may be coupled to the second catheter (210) such that the second catheter may pass through an inner chamber of the inflatable member (207). A first electrode (213) may be disposed on a surface of a distal portion (217) of the first catheter (203) and may be either separated from or attached to a proximal portion of the inflatable member (207). A second electrode (220) may be disposed on a distal portion (223) of the second catheter (210) and may be either separated from or attached to a distal portion of the inflatable member (207). The distal portion (223) of the second catheter (217) may be linearly moveable and about a portion distal to the first catheter (203). In some embodiments, the second electrode (223) may be moveable relative to the first electrode (213). A proximal portion of the inflatable member (207) may be coupled to the distal portion of the first catheter (203).

Figure 2B:
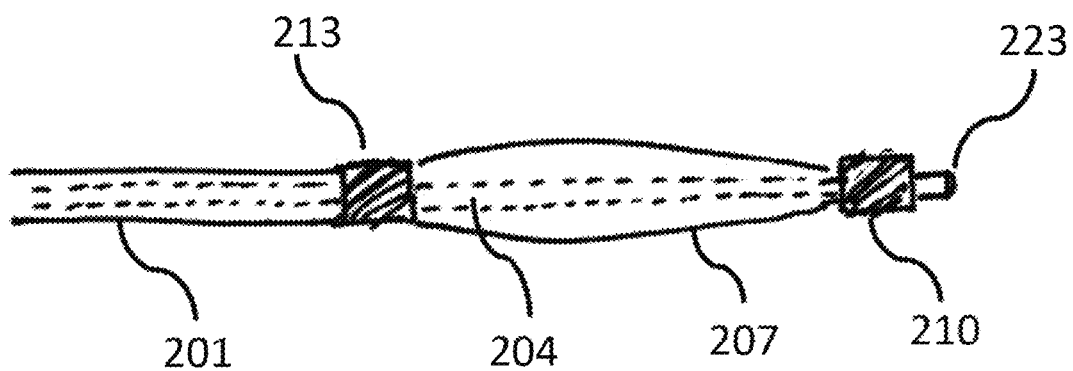
FIG. 2B is a side view of an ablation device depicted in FIG. 2A in a deflated state, according to embodiments.

A proximal end of the inflatable member (207) may be attached proximal to a distal end of the first catheter (203). The first electrode (213) may be disposed on the first catheter (203) just proximal to the proximal end of the inflatable member (207). In FIGS. 2A-2B, the second catheter or tubular lumen (210) is shown as extending from the distal end (217) of the first catheter (203) and out of a distal end of the inflatable member (207). The second electrode (220) is disposed on a surface of the second catheter (210) proximal to the distal end (223) of the second catheter (210). The distal end of the inflatable member (207) may be attached to the second catheter (210) just proximal to the second electrode (220).

In some embodiments, a handle (not shown) may be coupled to a proximal portion of the ablation device (200) and may include a bending mechanism (not shown) (e.g., knob, switch, pull wires) configured to deflect a portion of the second catheter (210) just proximal to the first catheter (203). For example, operation of a pull wire of the handle may increase or decrease a curvature in a distal portion of the first catheter. A fluid port can attach to the handle for infusion of fluid such as distilled water or deionized water to inflate the inflatable member. In embodiments, the handle can incorporate a deployment mechanism configured to advance and retract the second catheter or guidewire lumen (210) such that a distance between the first electrode (213) and the second electrode (220) may be varied. For example, after the inflatable member is positioned suitably in a pulmonary vein, it can be inflated and well-apposed in the vein. Subsequently, the first electrode (213) and the second electrode (220) may be brought closer together by retracting the second catheter (210) relative to the first catheter (203). In this manner, the device may be configured for PEF ablation delivery.

The inflatable member (207) may be configured to transition between a first configuration (e.g., deflated inflatable member in FIG. 2B) and a second configuration (e.g., inflated inflatable member in FIG. 2A). The inflatable member (207) in the first configuration may be in a compact, deflated state suitable for advancement through vasculature. For example, the inflatable member (207) in the first configuration may be substantially empty of fluid, such as sterile distilled or deionized water or saline. In some embodiments, fluid may enter the inflatable member (207) via an infusion port of a handle coupled to the ablation device. The inflatable member (207) in the second configuration may hold a volume of saline or distilled or deionized water that fills and inflates the inflatable member (207) to an appropriate size and shape (e.g., having a diameter to contact a diameter of a pulmonary vein) under pressure from a syringe or other infusion device. The inflatable member (207) may transition to an intermediate configuration between the first and second configuration as necessary, for example, to conform to a lumen or advance the device through vasculature. In some embodiments, the inflatable member may be pressurized using one or more of a hand-operated syringe, pump, infusion device, combinations thereof, and the like. In some embodiments, an infusion pressure may be between about 2 psi and about 20 psi.

Although FIGS. 2A and 2B depict an ablation device having one proximal electrode (213) and one distal electrode (223), it should be appreciated that more electrodes can be used in other embodiments. For example, the first electrode (213) may include a set of electrodes (e.g., two or more proximal electrodes formed along a length of the first catheter). Likewise, the second electrode (220) may include a set of electrodes (e.g., two or more distal electrodes formed along a length of the second catheter). In some embodiments, a diameter of the electrodes (213, 220) may be between about 1 mm and about 6 mm, including all values and sub-ranges in between. A length of the electrodes (213, 220) (measured along a longitudinal axis of the first and second catheters) may be between about 1 mm and about 8 mm, including all values and sub-ranges in between. In some embodiments, a set of electrodes disposed on a surface of the first catheter (e.g., a set of two or more proximal electrodes (213)) may be spaced apart by between about 0.5 mm and about 9 mm, including all values and sub-ranges in between. In some embodiments, a set of electrodes disposed on a surface of the second catheter (e.g., a set of two or more distal electrodes (220)) may be spaced apart by between about 0.5 mm and about 9 mm, including all values and sub-ranges in between. In some embodiments, the inflatable member in a second configuration (e.g., inflated, deployed) may have an outer diameter (e.g., maximum width) of between about 20 mm and about 40 mm, including all values and sub-ranges in between. In some embodiments, the inflatable member in a first configuration (e.g., deflated, undeployed state) may have a length (measured along a longitudinal axis of the second catheter) of between about 10 mm and about 80 mm, including all values and sub-ranges in between, when the first and second electrodes (213, 220) are maximally separated.

Figure 3:
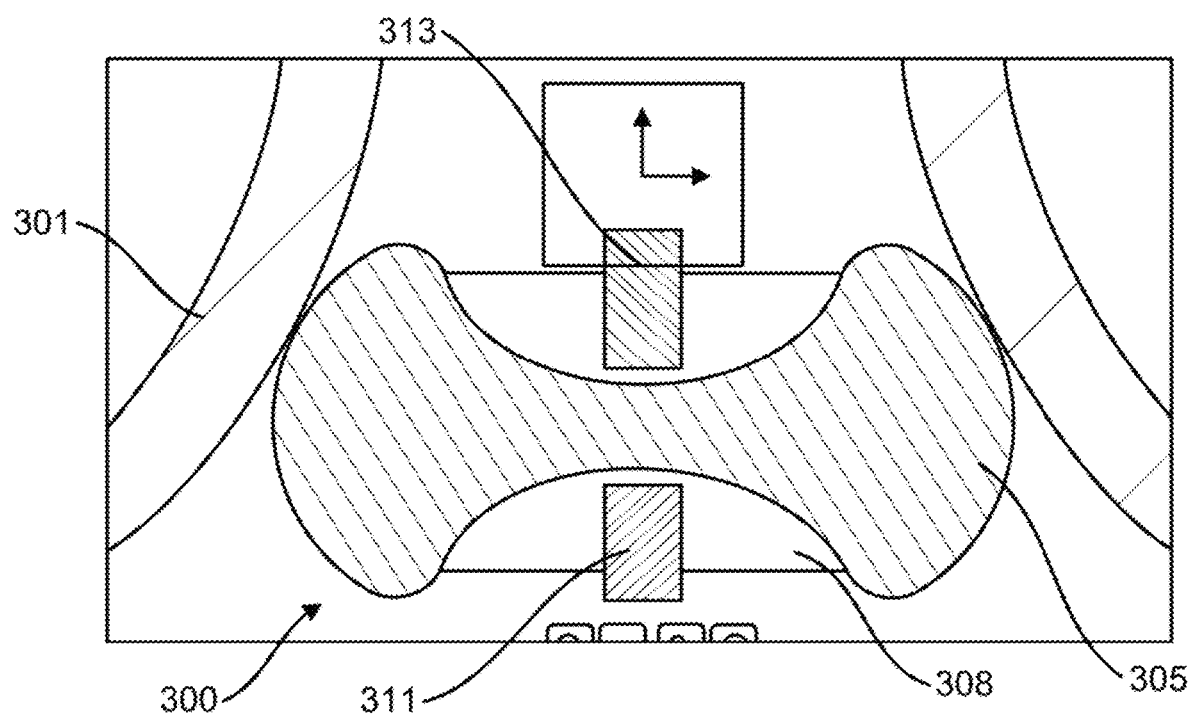
FIG. 3 is a cross-sectional side view of an ablation device disposed in a pulmonary vein, according to embodiments.

FIG. 3 illustrates an ablation device (300) including an inflatable member (305) (e.g., structurally and/or functionally similar to the ablation device (110, 200)) in a second configuration (e.g., inflated) and deployed coaxially at an ostium of a pulmonary vein (301). The ablation device (300) includes a first electrode (311) coupled to a proximal end of the inflatable member (305) and a second electrode (313) coupled to a distal end of the inflatable member (305). A first catheter and a second catheter (e.g., a guidewire catheter defining a lumen), similar to those described herein, are not shown in FIG. 3 for the sake of clarity. In FIG. 3, the second catheter or guidewire lumen (not shown) has been retracted relative to the first catheter such that the first electrode (311) and second electrode (313) are minimally separated. When the inflatable member is in the second configuration and the first and second electrodes (311, 313) are retracted towards each other, a central region (308) of the inflatable member (305) may likewise be retracted towards each other or pulled in such that the proximal and distal ends of the inflatable member (305) are brought closer together. In this manner, the first and second electrodes (311, 313) may be at least partially surrounded by portions of the inflatable member (305) (where the balloon is folded inward).

Figure 4A:
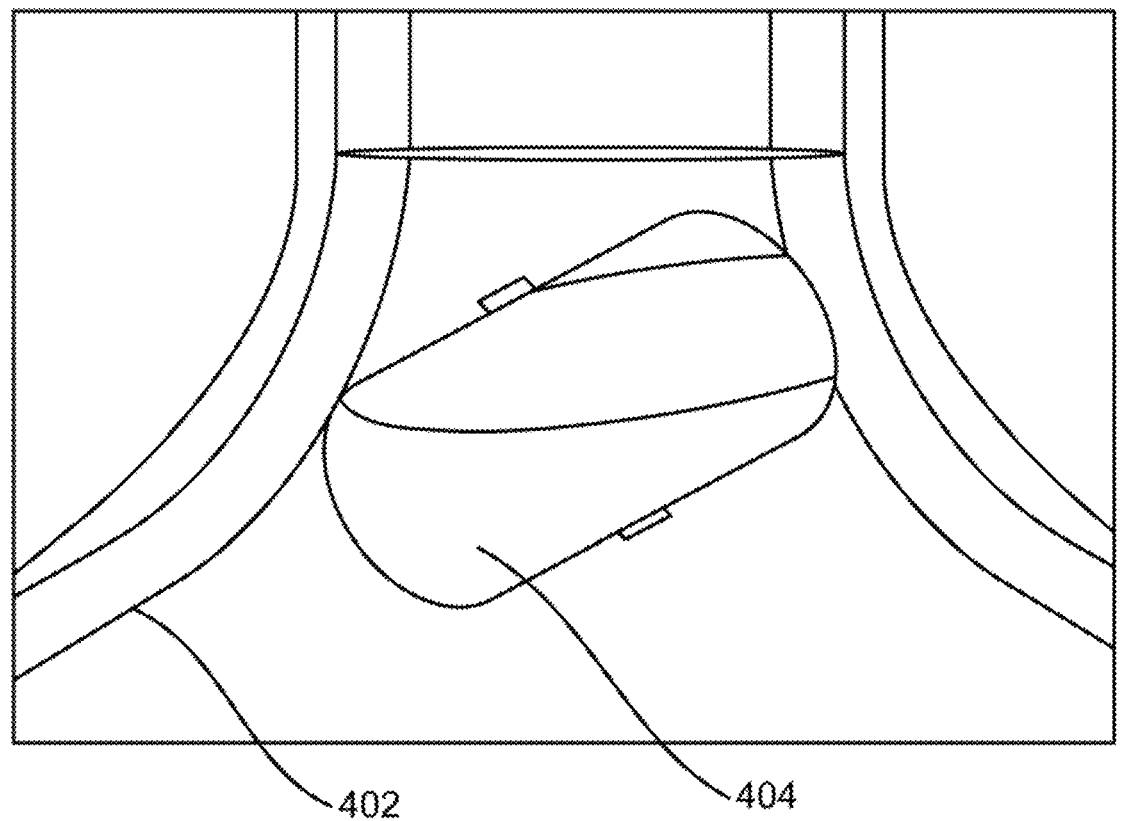
FIG. 4A is a cross-sectional side view of an ablation device disposed in a pulmonary vein, according to embodiments.
Figure 4B:
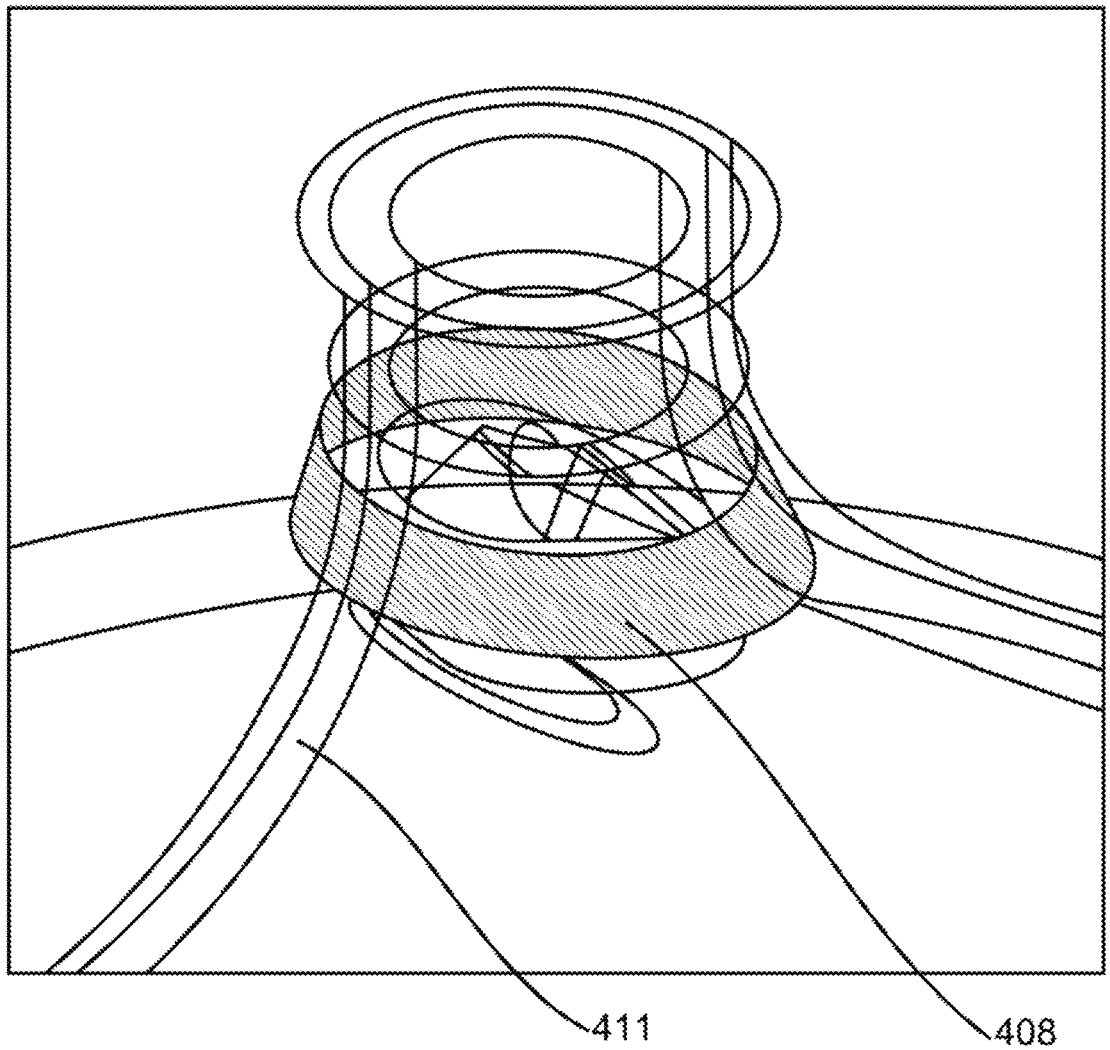
FIG. 4B is a perspective view of an ablation zone associated with the ablation device depicted in FIG. 4A when disposed in a pulmonary vein, according to embodiments.

FIG. 4A is a cross-sectional side view of an ablation device (400) (e.g., structurally and/or functionally similar to the ablation device (110, 200, 300)) disposed at a pulmonary vein ostium (402). In particular, a longitudinal axis of the ablation device (400) is disposed at an angle relative to a longitudinal axis of the pulmonary vein. FIG. 4B is a cross-sectional perspective view of an ablation zone (408) of the ablation device depicted in FIG. 4A disposed in a pulmonary vein (411). The ablation device (400) may include an inflatable member (404) and a first electrode (e.g., electrode proximal to the inflatable member (404)) and a second electrode (e.g., electrode distal to the inflatable member (404)). The first and second electrodes may be configured as an anode-cathode pair to deliver ablation energy to tissue. The ablation zone (408) may form a continuous ring-like shape on the pulmonary vein ostium (402) when the anode-cathode pair delivers energy that exceeds a threshold value required to generate irreversible electroporation.

Figure 5A:
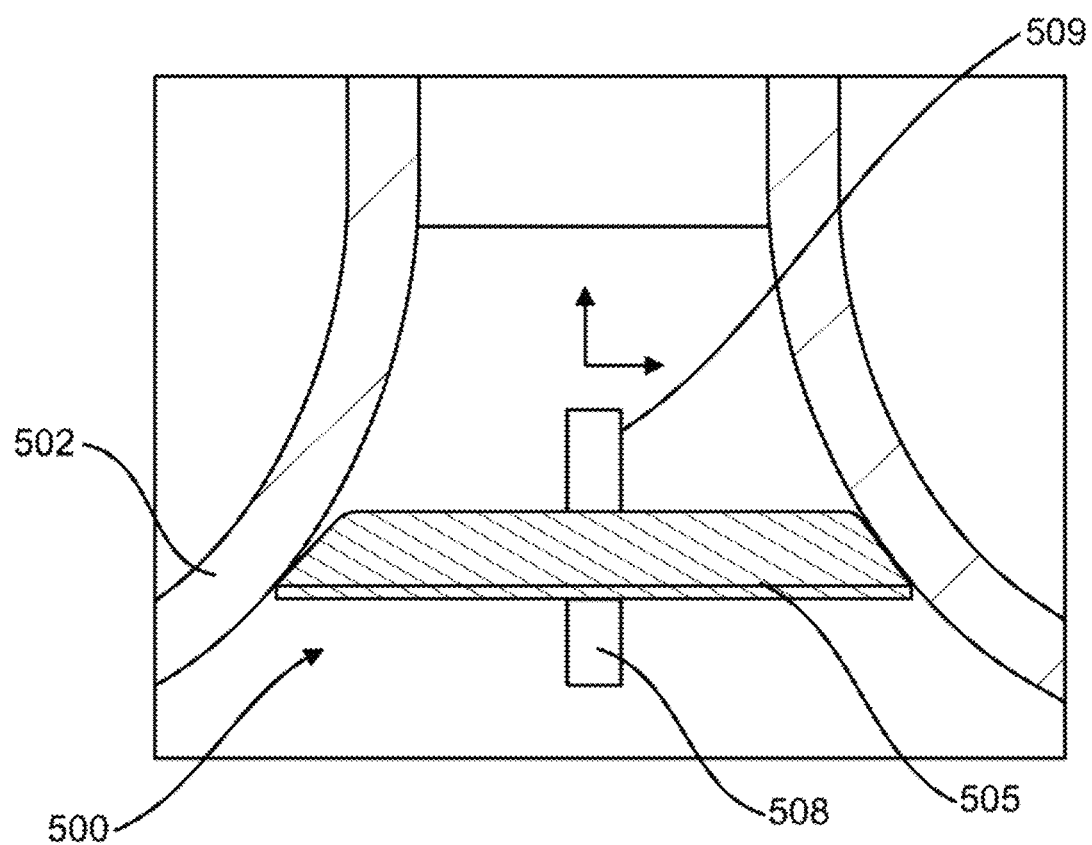
FIG. 5A is a cross-sectional side view of an ablation device disposed in a pulmonary vein, according to embodiments.
Figure 5B:
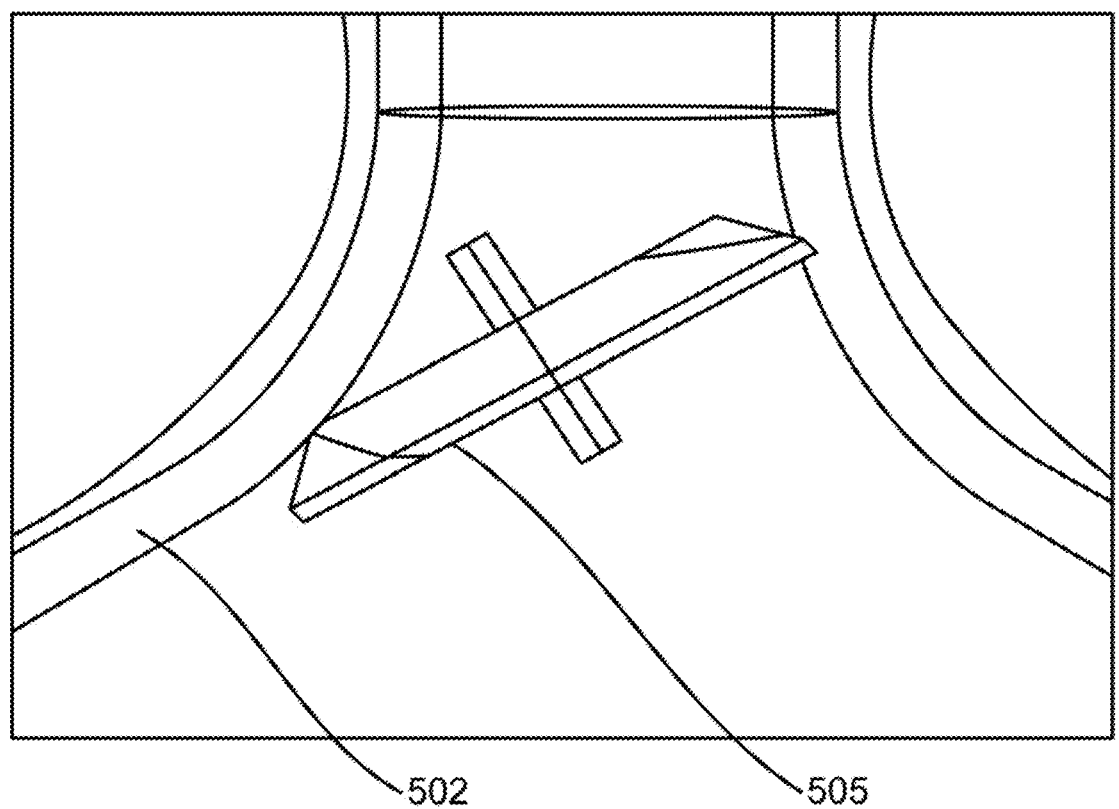
FIG. 5B is a cross-sectional side view of the ablation device depicted in FIG. 5A disposed in a pulmonary vein.

FIG. 5A is a cross-sectional side view of an ablation device (500) (e.g., structurally and/or functionally similar to the ablation device (110, 200, 300, 400)) disposed in a pulmonary vein ostium (502) (e.g., deployed coaxially). The ablation device (500) includes a first electrode (508) coupled to a proximal end of the inflatable member (505) and a second electrode (509) coupled to a distal end of the inflatable member (505). Alternatively or in addition, the first and second electrodes may be respectively coupled to the distal portion of the first catheter proximal to the inflatable member and to the distal portion of the second catheter/guidewire lumen distal to the inflatable member. A first catheter or outer shaft and a second catheter or inner shaft (e.g., a guidewire lumen), similar to those described herein, are not shown in FIGS. 5A-5B for the sake of clarity. In FIG. 5A, the inflatable member (505) when inflated may form a frustum shape (e.g., a trapezoidal shape when viewed in lateral section). In some embodiments, a diameter of the inflatable member (505) at its widest portion may be between about 20 mm and about 40 mm, including all values and sub-ranges in between. A length of the inflatable member (505) (measured along a longitudinal axis of the first and second catheter) when fully deployed may be between about 3 mm and about 30 mm, including all values and sub-ranges in between. FIG. 5B is a cross-sectional side view of the ablation device (500) depicted in FIG. 5A where a longitudinal axis of the ablation device (500) is disposed at an angle relative to a longitudinal axis of the pulmonary vein (502).

Figure 6A:
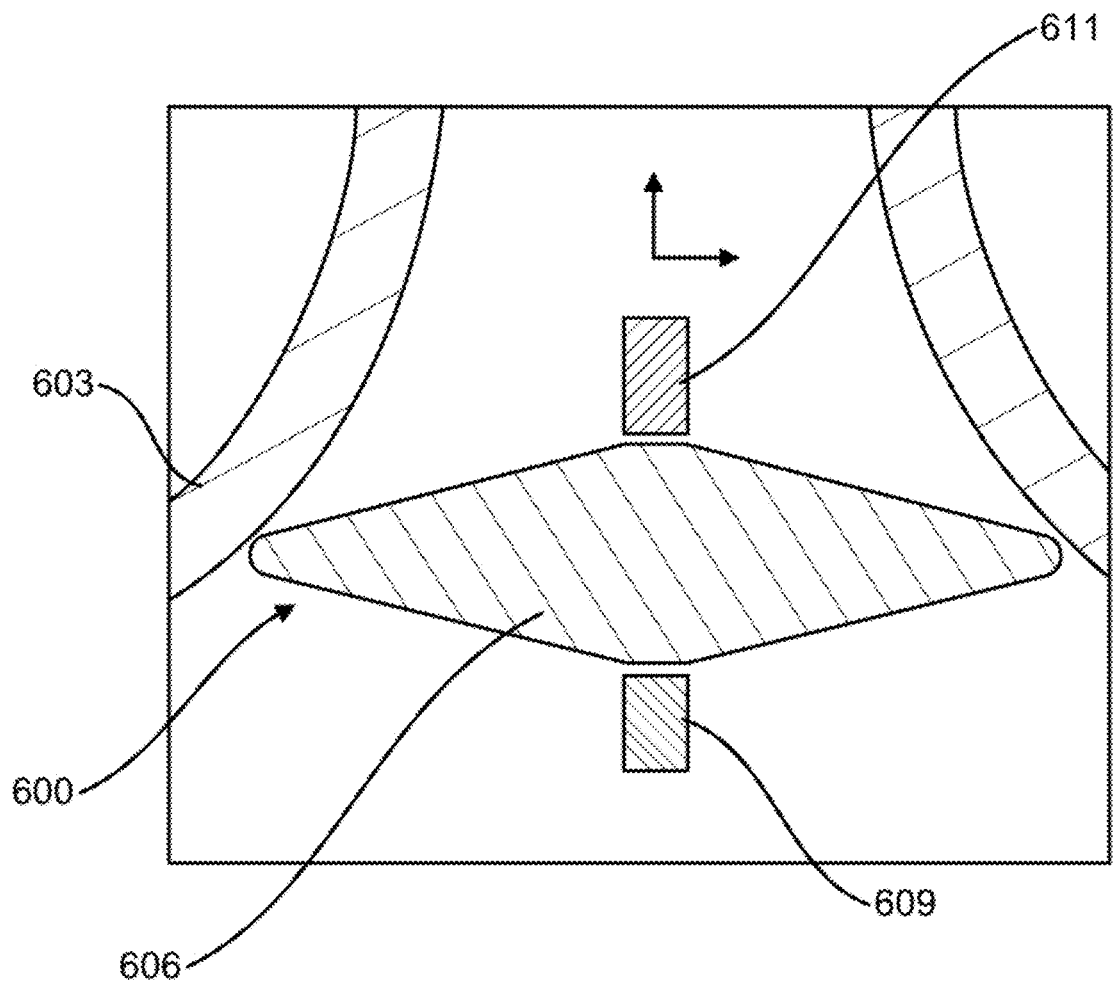
FIG. 6A is a cross-sectional side view of an ablation device disposed in a pulmonary vein, according to embodiments.
Figure 6B:
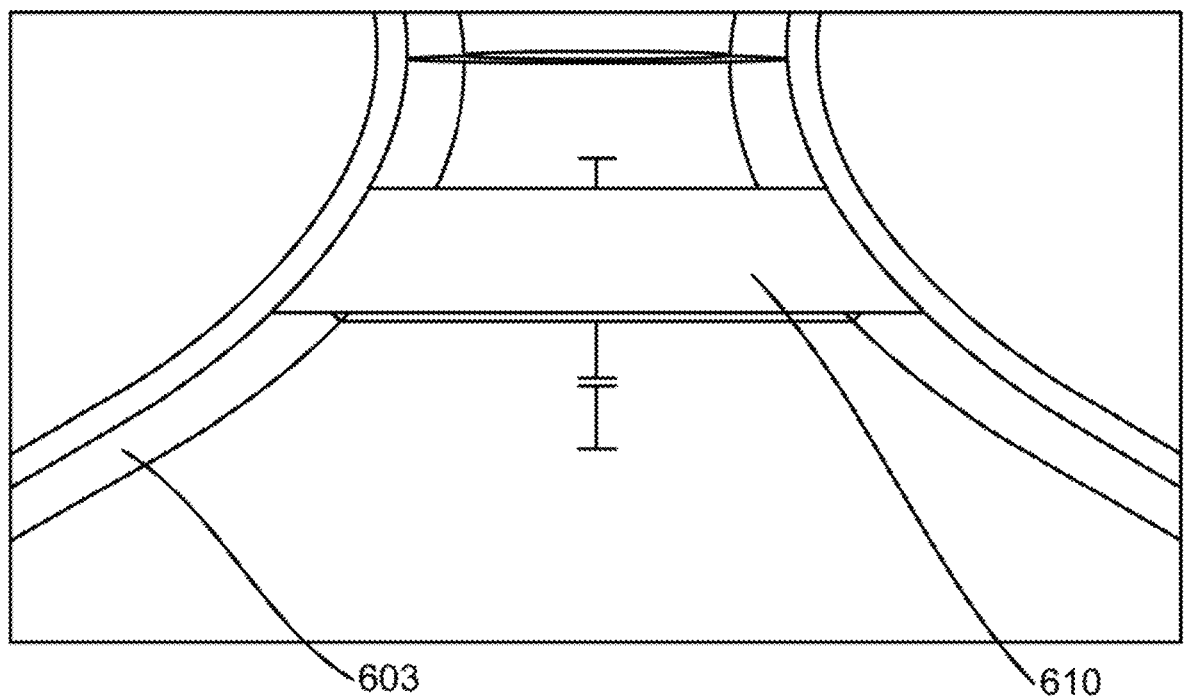
FIG. 6B is a cross-sectional side view of an ablation zone of the ablation device depicted in FIG. 6A disposed in a pulmonary vein.

FIG. 6A is a cross-sectional side view of an ablation device (600) (e.g., structurally and/or functionally similar to the ablation device (110, 200, 300, 400, 500)) disposed in a pulmonary vein ostium (603) (e.g., deployed coaxially). The ablation device (600) includes a first electrode (609) coupled to a proximal end of the inflatable member (606) and a second electrode (611) coupled to a distal end of the inflatable member (606). Additionally or alternatively, the first and second electrodes may be respectively coupled to the distal portion of the first catheter/outer shaft proximal to the inflatable member and to the distal portion of the second catheter/guidewire lumen distal to the inflatable member. A first catheter/outer shaft and a second catheter (e.g., an inner shaft defining a lumen), similar to those described herein, are not shown in FIGS. 6A-6B for the sake of clarity. The inflatable member (606) in the inflated configuration may form a rhombus-like shape in a lateral view, as shown in FIG. 6A. FIG. 6B is a lateral section view of an ablation zone (610) of the ablation device (600) depicted in FIG. 6A disposed in a pulmonary vein (603). The first and second electrodes (609, 611) may be configured as an anode-cathode pair to deliver ablation energy to tissue. The ablation zone (610) may form a ring-like shape on the pulmonary vein ostium (603) when the anode-cathode pair delivers energy that exceeds a threshold value required to generate irreversible electroporation.

Figure 7:
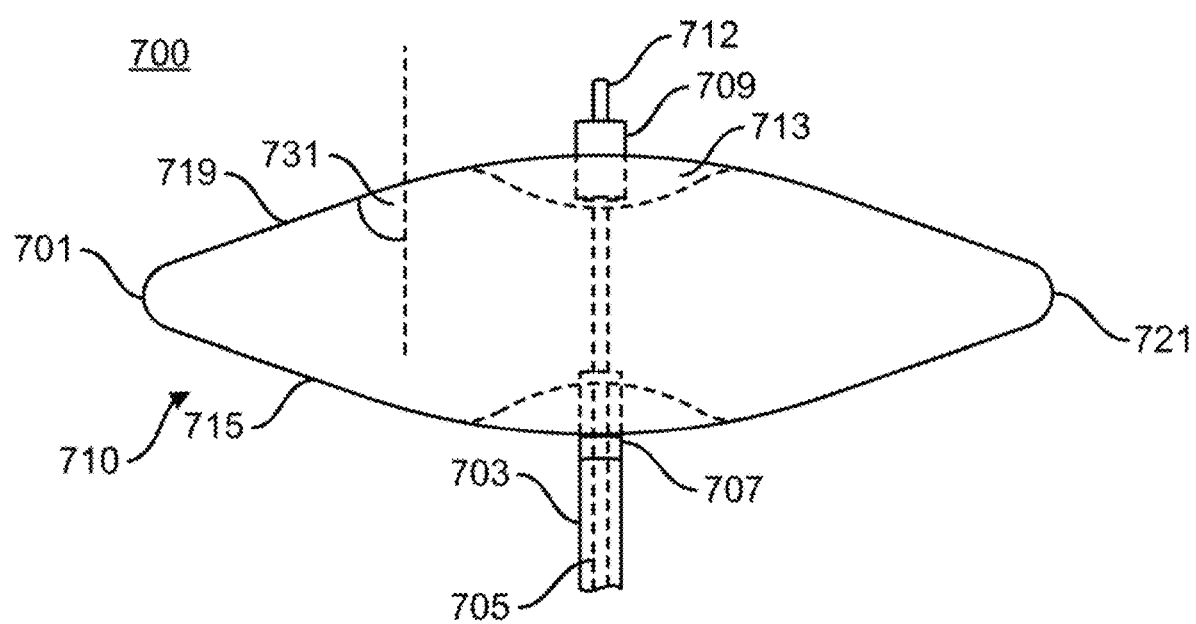
FIG. 7 is a side view of an ablation device, according to embodiments.

FIG. 7 is a schematic cross-sectional side view of an ablation device (700) (e.g., structurally and/or functionally similar to the ablation device (110, 200, 300, 400, 500, 600)). The ablation device (700) may include a first catheter (703) (e.g., outer catheter shaft) defining a lumen, a second catheter (705) (e.g., an inner shaft defining a lumen), and an inflatable member (710). The second catheter (705) may be disposed within a lumen of the first catheter (703) and a chamber of the inflatable member (710) where the second catheter (705) may be slideable relative to the first catheter (703). The inflatable member (e.g., balloon) (710) may be coupled to the second catheter (705) such that the second catheter (705) may pass through an inner chamber of the inflatable member (710). A first electrode (707) may be disposed on a surface of a distal portion of the first catheter (703) and just proximal to the inflatable member (710). A second electrode (709) may be disposed on a distal portion (712) of the second catheter (705) and just distal to the inflatable member (710). The second catheter (705) may be linearly slideable relative to the first catheter (703). Thus, the second electrode (709) may be linearly slideable relative to the first electrode (707). A proximal portion of the inflatable member (710) may be coupled to the distal portion of the first catheter (703). In FIG. 7, the inflatable member (710) may form an approximately rhombus-like shape.

In some embodiments, the ablation device (700) may include a handle (not shown) coupled to a proximal portion of the ablation device (700) and may include a mechanism (not shown) (e.g., knob, switch, pull wires) configured to advance and retract the second catheter or guidewire (705) relative to the first catheter (703) such that a distance between the first electrode (707) and the second electrode (709) may be varied. For example, the first electrode (707) and the second electrode (709) may be brought closer together by retracting the second catheter (705) relative to the first catheter (703). In FIG. 7, a central portion (713) of a distal end of the inflatable member (710) is shown as retracted toward a proximal end of the inflatable member (710).

When suitably inflated, a proximal major portion (715) and a distal major portion (719) of the inflatable member (710) may be angled relative to a longitudinal axis of the first catheter (703) such that a surface of the inflatable member (710) forms an angle (731) with respect to the longitudinal axis that is greater than about 45 degrees. In some embodiments, a middle portion (721) of the inflatable member (710) may be relatively short compared to the major portions (715, 719).

Although FIG. 7 depicts an ablation device having one proximal electrode (707) and one distal electrode (709), it should be appreciated that more electrodes can be used in other embodiments. For example, the first electrode (707) may include a set of electrodes (e.g., two or more proximal electrodes). Likewise, the second electrode (709) may include a set of electrodes (e.g., two or more distal electrodes). In some embodiments, a diameter of the electrodes (707, 709) may be between about 1 mm and about 6 mm, including all values and sub-ranges in between. A length of the electrodes (707, 709) (measured along a longitudinal axis of the first and second catheters) may be between about 1 mm and about 8 mm, including all values and sub-ranges in between. In some embodiments, a set of electrodes disposed on a surface of the first catheter (703) (e.g., a set of two or more proximal electrodes (707)) may be spaced apart by between about 0.5 mm and about 9 mm, including all values and sub-ranges in between. In some embodiments, a set of electrodes disposed on a surface of the second catheter (705) (e.g., a set of two or more distal electrodes (709)) may be spaced apart by between about 0.5 mm and about 9 mm, including all values and sub-ranges in between. In some embodiments, the inflatable member (710) in a second configuration (e.g., inflated) may have an outer diameter of between about 20 mm and about 40 mm, including all values and sub-ranges in between. In some embodiments, the inflatable member (710) in a first configuration (e.g., deflated, undeployed state) may have a length (measured along a longitudinal axis of the second catheter) of between about 10 mm and about 80 mm, including all values and sub-ranges in between, when the first and second electrodes (707, 709) are maximally separated. In a fully deployed state with the second catheter (705) retracted for minimal separation between the first and second electrodes (707, 709), a length of the inflatable member (710) (measured along a longitudinal axis of the first catheter (703) may be between about 3 mm and about 30 mm, including all values and sub-ranges in between.

Figure 8:
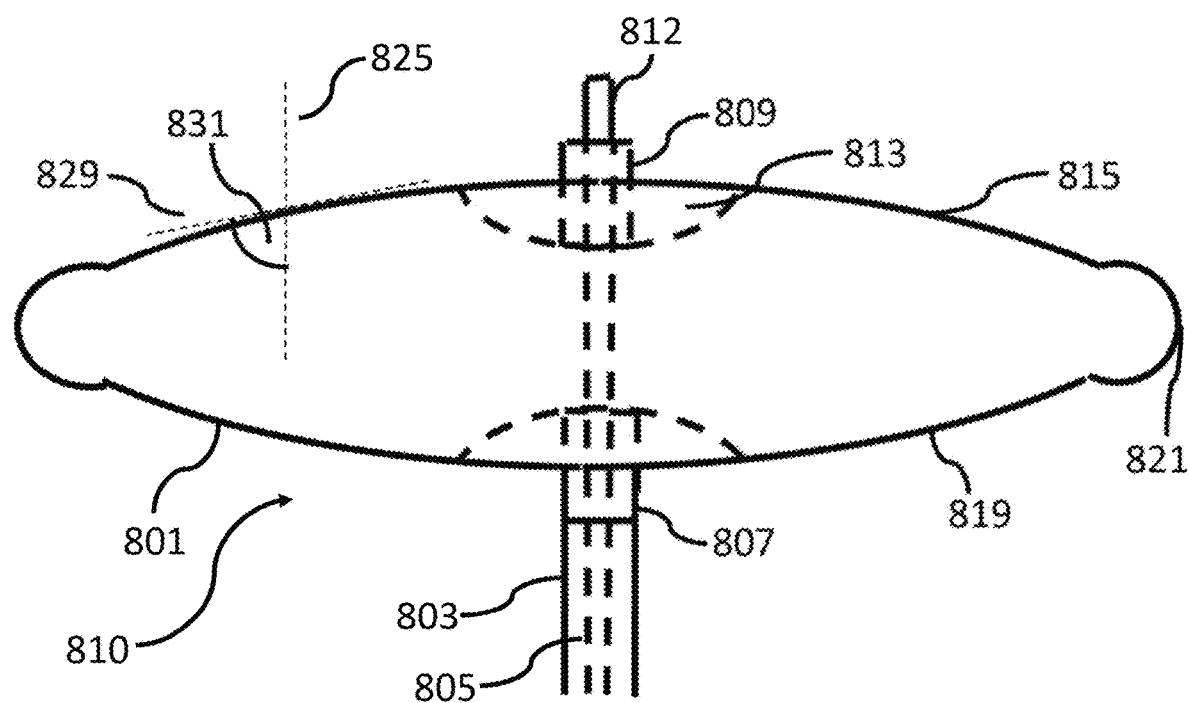
FIG. 8 is a side view of an ablation device, according to embodiments.

FIG. 8 is a schematic cross-sectional side view of an ablation device (800) (e.g., structurally and/or functionally similar to the ablation device (110, 200, 300, 400, 500, 600, 700)). The ablation device (800) may include a first catheter (803) (e.g., outer catheter shaft) defining a lumen, a second catheter (805) (e.g., an inner shaft defining a guidewire lumen), and an inflatable member (810). The second catheter (805) may be disposed within a lumen of the first catheter (803) and a chamber of the inflatable member (810) where the second catheter (805) may be slidable relative to the first catheter (803). The inflatable member (e.g., balloon) (810) may be coupled to the second catheter (805) such that the second catheter (805) may pass through an inner chamber of the inflatable member (810). A first electrode (807) may be disposed on a surface of a distal portion of the first catheter (803) and just proximal to the inflatable member (810). A second electrode (809) may be disposed on a distal portion (812) of the second catheter (805) and just distal to the inflatable member (810). The second catheter (805) may be linearly slideable relative to the first catheter (803). Thus, the second electrode (809) may be slideable relative to the first electrode (807). A proximal portion of the inflatable member (810) may be coupled to the first catheter (803) and a distal portion of the inflatable member (810) may be coupled to the second catheter (805) such that the second catheter (805) may pass through an inner chamber of the inflatable member (810).

In some embodiments, the ablation device (800) may include a handle (not shown) coupled to a proximal portion of the ablation device (800) and may include a mechanism (not shown) (e.g., knob, switch, pull wires) configured to advance and retract the second catheter (805) such that a distance between the first electrode (807) and the second electrode (809) may be varied. For example, the first electrode (807) and the second electrode (809) may be brought closer together by retracting the second catheter or guidewire (805) relative to the first catheter (803). In FIG. 8, a central portion (813) of a distal end of the inflatable member (810) is shown as retracted toward a proximal end of the inflatable member (810) using a handle and a bending mechanism as described herein.

When suitably inflated, a proximal major portion (815) and a distal major portion (819) of the inflatable member (810) may be gently curved with the surface locally having an angle relative to a longitudinal axis of the first catheter (803) such that a surface of the inflatable member (810) locally forms an angle (831) with respect to the longitudinal axis. In some embodiments, a middle portion (821) of the inflatable member (810) may be relatively short in length compared to the major portions (815, 819). In some embodiments, the major portions (815, 819) may be gently curved with steep slopes with respect to the longitudinal axis (825) of the first catheter (803). In FIG. 8, a local tangent (829) to a surface of the inflatable member (i.e., the component of the local tangent in the plane defined by radial and axial directions) may form an angle (831) with the longitudinal axis (825) that is greater than about 45 degrees.

In some embodiments, a middle portion (821) of the inflatable member (810) may be relatively short in length compared to the major portions (815, 819). When the inflatable member (810) is inflated (e.g., suitably pressurized), the middle portion (821) may bulge as shown in FIG. 8. In some embodiments, the middle portion (821) of the inflatable member (810) may be constructed of thinner material compared to the major portions (815, 819). For example, the thickness of a wall of an inflatable member (810) of the major portions (815, 819) may be at least 20% larger than the thickness of the wall at the middle portion (821). In some embodiments, the thickness of a wall of an inflatable member (810) of the major portions (815, 819) may be at least 50% larger than the thickness of the wall at the middle portion (821). In some embodiments, the thickness of a wall of an inflatable member (810) of the major portions (815, 819) may be at least 100% larger than the thickness of the wall at the middle portion (821).

Figure 10:
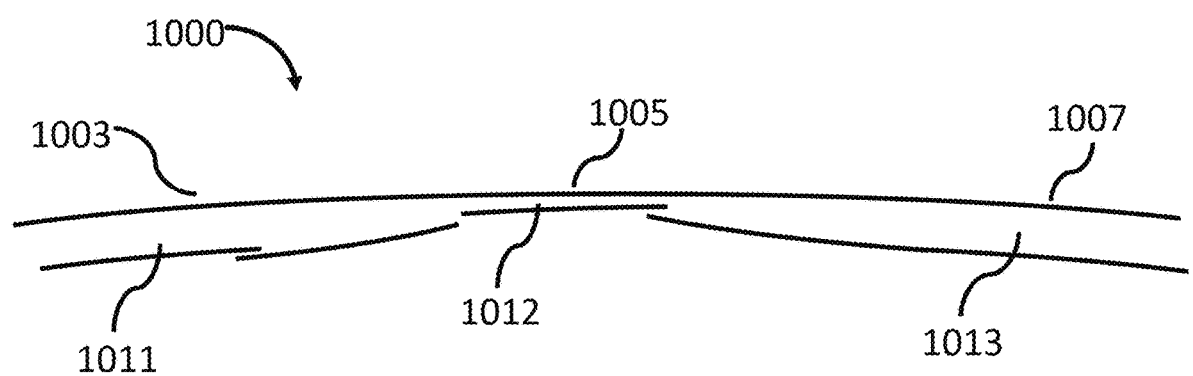
FIG. 10 is a schematic side view of a portion of a wall of an inflatable member of an ablation device, according to embodiments.

FIG. 10 is a schematic side view of portion of the wall (1000) of an uninflated inflatable member including a proximal portion (1003), a middle portion (1005), and a distal portion (1007). FIG. 10 illustrates schematically that the thickness (1011) of the proximal portion and thickness (1013) of the distal portion may be significantly larger than the thickness (1012) of the middle portion.

Figure 11:
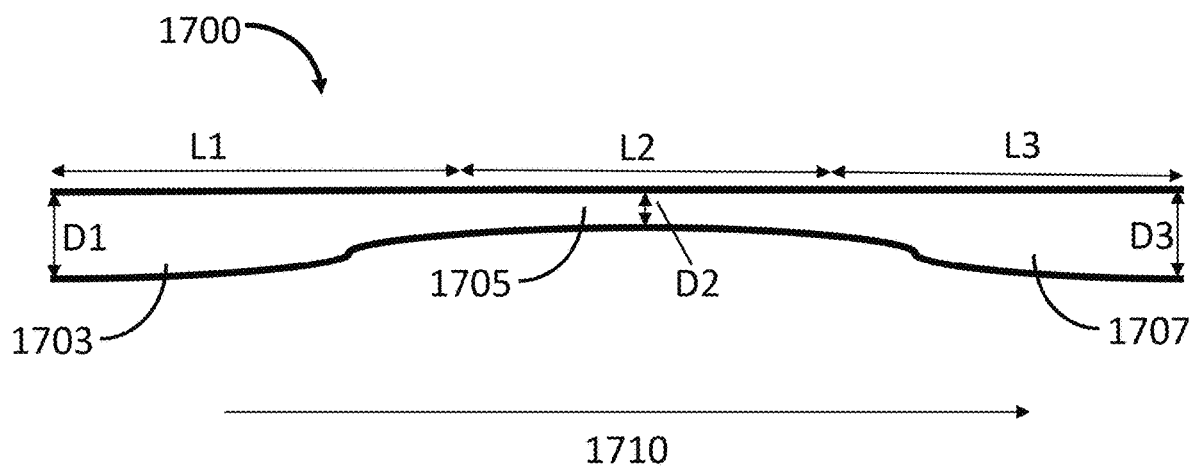
FIG. 11 is a schematic side view of a portion of a wall of an inflatable member of an ablation device, according to embodiments.

FIG. 11 is a schematic side view of a portion of a wall (1700) of an inflatable member of an ablation device, including a proximal portion (1703), a middle portion (1705), and a distal portion (1707), as arranged along a longitudinal or central axis (1710) of the inflatable member. Any of the inflatable members described herein (e.g., inflatable members 207, 305, 404, 505, 606, etc.) can have a wall that is structurally and/or functionally similar to the wall (1700) depicted in FIG. 11. The proximal portion (1703) of the wall (1700) can have a length L1 extending along the longitudinal axis (1710), the middle portion (1705) of the wall (1700) can have a length L2 extending along the longitudinal axis (1710), and the distal portion (1707) of the wall (1700) can have a length L3 extending along the longitudinal axis (1710). The lengths L1 and L3 can be greater than L2, with the ratios L1/L2 and L3/L2 being greater than three.

As depicted in FIG. 11, the proximal portion (1703) of the wall (1700) of the inflatable member can have a maximum thickness D1, the middle portion (1705) of the wall (1700) can have a minimum thickness D2, and the distal portion (1707) of the wall (1700) can have a maximum thickness D3. In some embodiments, thicknesses D1 and D3 of the proximal and distal portions (1703, 1707), respectively, can be equal to one another (or about equal to one another), and the thickness D2 of the middle portion (1705) can be equal to or less than about a third of the thicknesses D1 and D3.

Although FIG. 8 depicts an ablation device having one proximal electrode (807) and one distal electrode (809), it should be appreciated that more electrodes can be used in other embodiments. For example, the first electrode (807) may include a set of electrodes (e.g., two or more proximal electrodes). Likewise, the second electrode (809) may include a set of electrodes (e.g., two or more distal electrodes). In some embodiments, a diameter of the electrodes (807, 809) may be between about 1 mm and about 6 mm, including all values and sub-ranges in between. A length of the electrodes (807, 809) (measured along a longitudinal axis of the first and second catheters) may be between about 1 mm and about 8 mm, including all values and sub-ranges in between. In some embodiments, a set of electrodes disposed on a surface of the first catheter (803) (e.g., a set of two or more proximal electrodes (807)) may be spaced apart by between about 0.5 mm and about 9 mm, including all values and sub-ranges in between. In some embodiments, a set of electrodes disposed on a surface of the second catheter (805) (e.g., a set of two or more distal electrodes (809)) may be spaced apart by between about 0.5 mm and about 9 mm, including all values and sub-ranges in between. In some embodiments, the inflatable member (810) in a second configuration (e.g., inflated) may have an outer diameter of between about 20 mm and about 40 mm, including all values and sub-ranges in between. In some embodiments, the inflatable member (810) in a first configuration (e.g., deflated, undeployed state) may have a length (measured along a longitudinal axis of the second catheter) of between about 10 mm and about 80 mm, including all values and sub-ranges in between, when the first and second electrodes (807, 809) are maximally separated. In a fully deployed state with the second catheter (805) retracted for minimal separation between the first and second electrodes (807, 809), a length of the inflatable member (810) (measured along a longitudinal axis of the first catheter (803) may be between about 3 mm and about 30 mm, including all values and sub-ranges in between.

Figure 9:
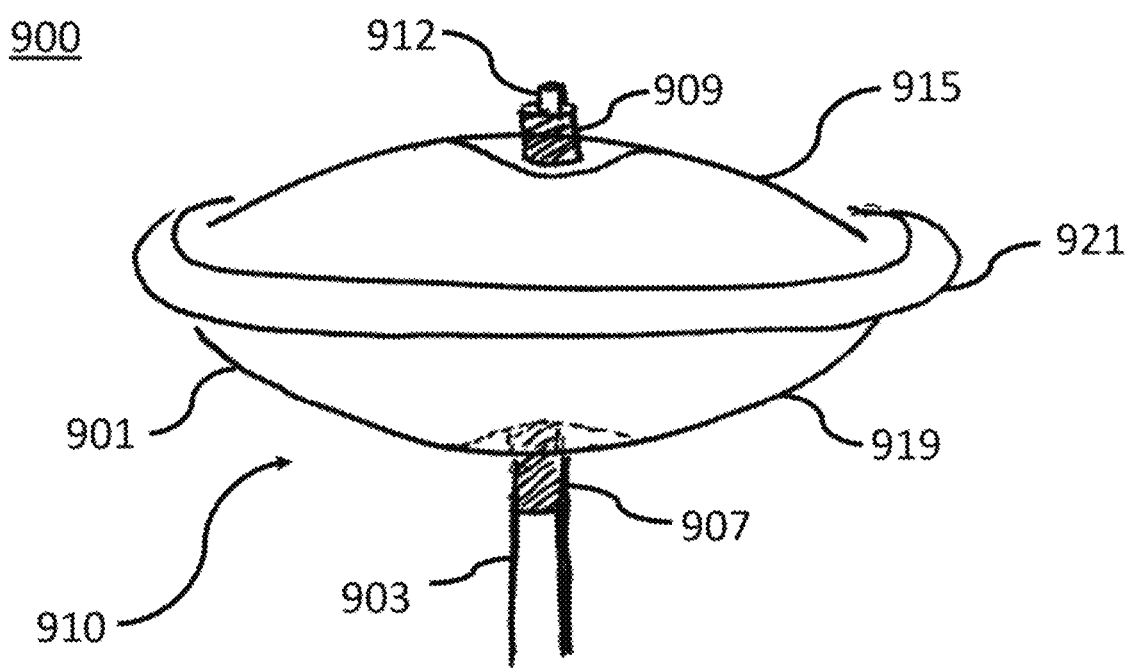
FIG. 9 is a perspective view of an ablation device, according to embodiments.

FIG. 9 is a perspective view of an ablation device (900) (e.g., structurally and/or functionally similar to the ablation device (110, (801))). In particular, the ablation device (900) corresponds to a perspective view of the ablation device (800) depicted in FIG. 8. The ablation device (900) may include a first catheter (903) (e.g., an outer catheter shaft) defining a lumen, a second catheter (e.g., inner shaft or guidewire lumen) (whose tip (912) is shown), and an inflatable member (910). The second catheter may be disposed within a lumen of the first catheter (903) and a chamber of the inflatable member (910) where the second catheter may be slideable relative to the first catheter (903). The inflatable member (e.g., balloon) (910) may be coupled to the second catheter such that the second catheter may pass through an inner chamber of the inflatable member (910). A first electrode (907) may be disposed on a surface of a distal portion of the first catheter (903) and separated from the inflatable member (910). A second electrode (909) may be disposed on a distal portion (912) of the second catheter and separated from the inflatable member (910). The second catheter may be linearly slideable relative to the first catheter (903). Thus, the second electrode (909) may be slideable relative to the first electrode (907). A proximal portion of the inflatable member (910) may be coupled to the distal portion of the first catheter (903). A proximal major portion (915) and a distal major portion (919) of the inflatable member (910) may be gently curved with the surface locally having an angle relative to a longitudinal axis of the first catheter (903). In some embodiments, a middle portion (921) of the inflatable member (910) may be relatively short in length compared to the major portions (915, 919). In some embodiments, the major portions (915, 919) may be gently curved with steep slopes with respect to a longitudinal axis of the first catheter (903).

Figure 12A:
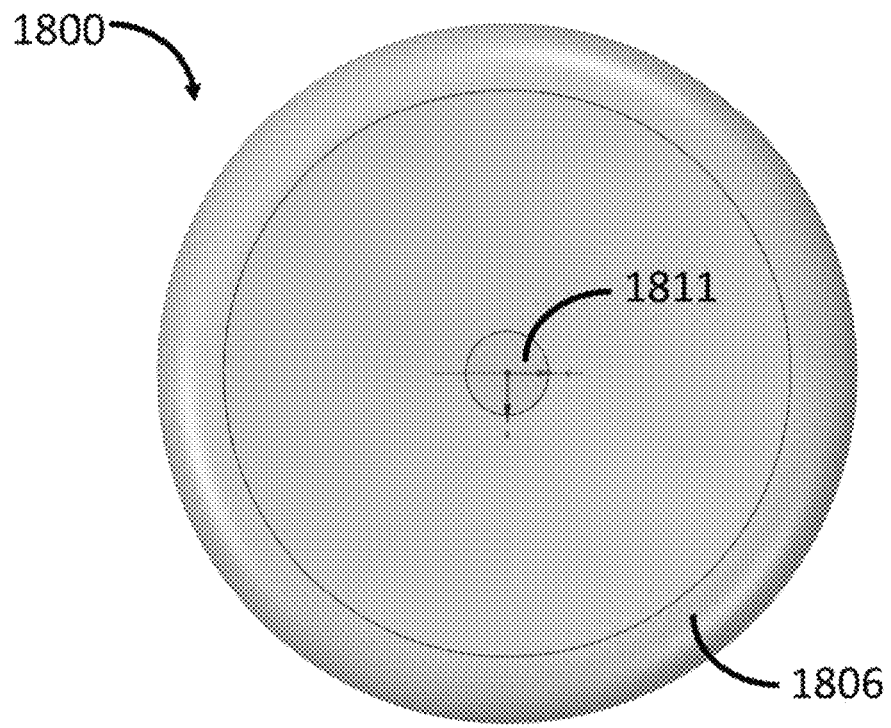
FIGS. 12A and 12B are different views of an ablation device, according to embodiments.
Figure 12B:
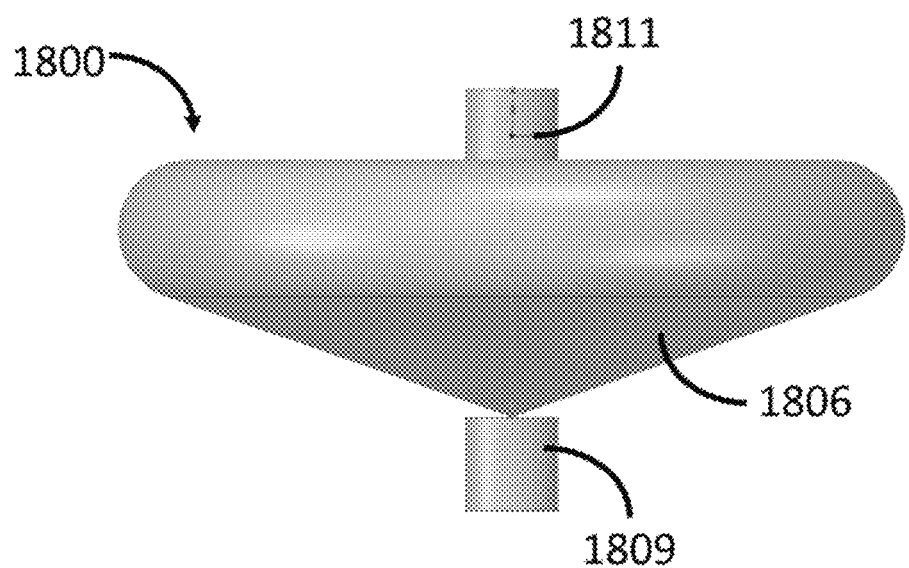

FIGS. 12A and 12B depict different views of an ablation device (1800), which can include components that are structurally and/or functionally similar to those of other ablation devices described herein. The ablation device (1800) can include a first electrode (1809) coupled to a proximal end of an inflatable member (1806), and a second electrode (1811) coupled to a distal end of the inflatable member (1806). In some embodiments, the second electrode (1811) can be coupled to an inner catheter or inner shaft or guidewire lumen, which in turn can be attached to a proximal handle (not depicted) for deploying the ablation device (1800). For example, the ablation device (1800) can be deployed by moving (e.g., pulling) the inner shaft proximally such that the second electrode (1811) is pulled toward the first electrode (1809) and the inflatable member (1806) is inflated. Once deployed, the ablation device (1800) can be locked in place with an appropriate locking mechanism, e.g., a locking mechanism disposed in the handle.

Figure 13:
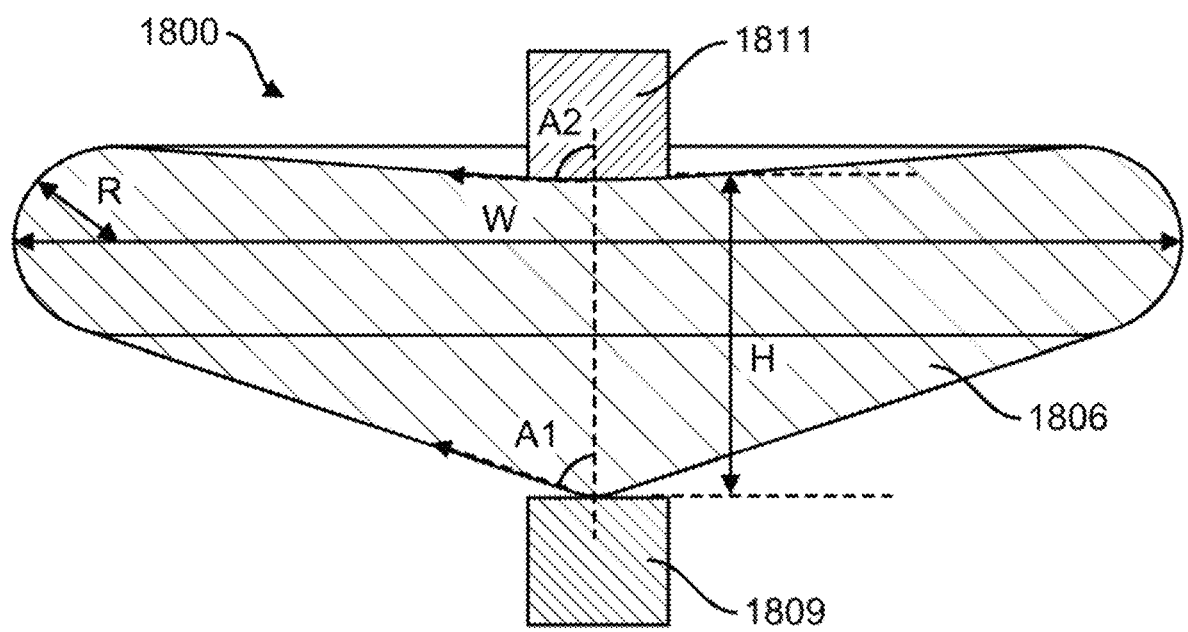
FIG. 13 is a cross-sectional side view of the ablation device depicted in FIGS. 12A and 12B.

The inflatable member (1806) in the inflated and deployed configuration can form a conical shape, such as shown in FIGS. 12A and 12B. In the deployed configuration, which is shown in more detail in FIG. 13, the inflatable member (1806) can have a maximum width W, a height H, and rounded sides (e.g., a side portion) with a radius of curvature R. In some embodiments, e.g., when the inflatable member (1806) is designed for use within a pulmonary vein of a heart, the width W can be less than about 40 mm, the height H can be less than about 25 mm, and the radius R can be less than about 15 mm.

Figure 14:
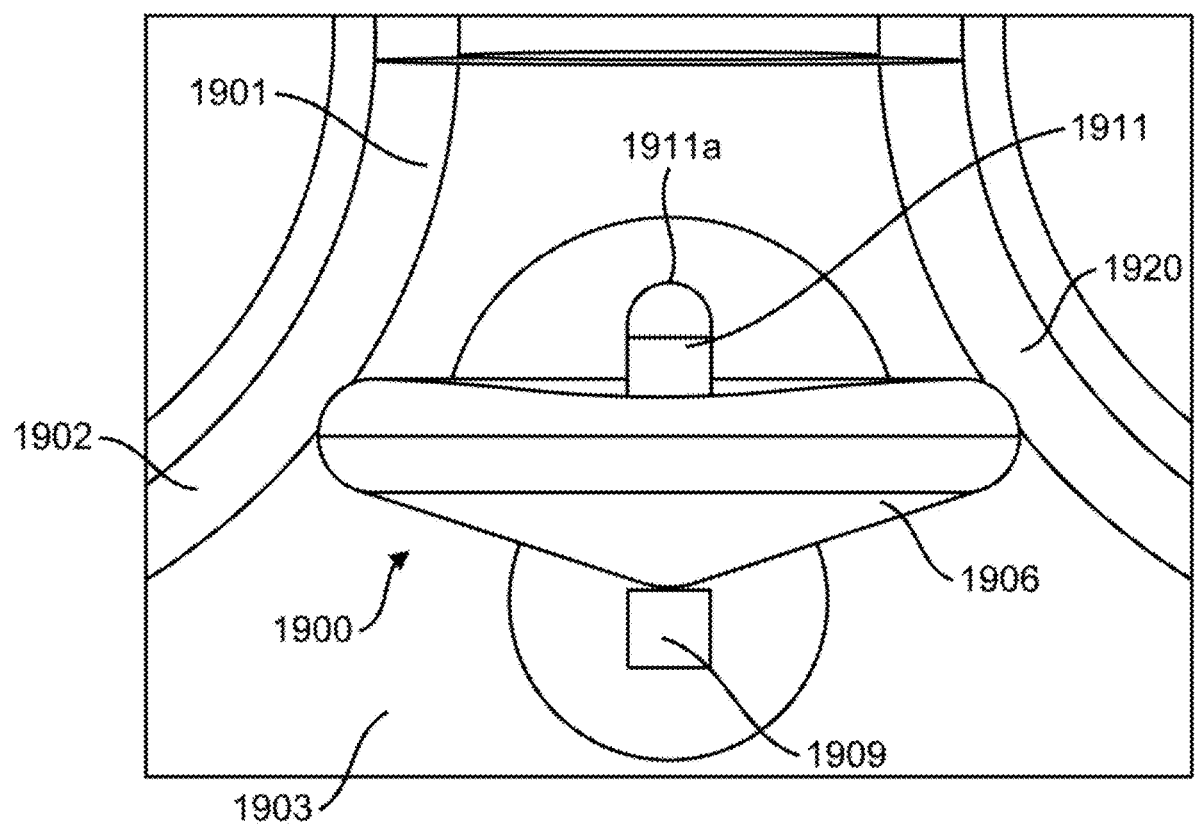
FIG. 14 is a cross-sectional side view of an ablation zone of the ablation device depicted in FIGS. 12A and 12B.

In some embodiments, the first and second electrodes (1809, 1811) can be structurally similar. For example, each of the first and second electrodes (1809, 1811) can have an outer diameter of about 1 mm to about 7 mm and a length of about 1 mm to about 15 mm. In some embodiments, the second electrode (1811) can have a rounded or atraumatic shape, e.g., as depicted in FIG. 14. The inner shaft or guidewire lumen can be used to pass a guidewire through it to assist with engaging a pulmonary vein, so that the catheter can be delivered to the target anatomy over the guidewire.

In some embodiments, a proximal portion of the inflatable member (1806) in the deployed configuration can be angled relative to a longitudinal axis of the ablation device (1800) by an angle A1, and a distal portion of the inflatable member (1806) can be angled relative to the longitudinal axis of the ablation device (1800) by an angle A2. In some embodiments, angle A2 can be greater than angle A1, such that the inflatable member (1806) when deployed has an asymmetrical shape. For example, in some embodiments, angle A1 can lie in the range between about 50 degrees and about 75 degrees, while angle A2 can be between about 80 degrees and about 90 degrees.

FIG. 14 depicts a cross-sectional side view of an ablation device (1900), e.g., including components that are structurally and/or functionally similar to those of other ablation devices described herein, while being disposed in a pulmonary vein ostium (1901) of a heart. In particular, similar to ablation device (1800), ablation device (1900) includes two electrodes (1909, 1911) disposed on opposite sides of an inflatable member (1906). Electrode (1911) disposed at a distal end of the inflatable member (1906) can have a rounded or atraumatic tip (1911a). When deployed, the inflatable member (1906) of the ablation device (1900) can have sides that engage with a wall (1902) of the pulmonary vein ostium (1901) and can hold the ablation device (1900) relative to the pulmonary vein ostium (1901). In the arrangement depicted in FIG. 14, the ablation device (1900) can be held such that its longitudinal axis is generally aligned with a longitudinal axis of the pulmonary vein ostium (1901), with a proximal side of the inflatable member (1906) facing the blood pool (1903) of the heart chamber. Alternatively, the ablation device (1900) can be held at other orientations with respect to the pulmonary vein ostium (1901) and generate different ablation zones within the surrounding tissue.

When oriented as shown in FIG. 14, the electrodes (1909, 1911) can generate an ablation zone (1920) when they are configured as an anode-cathode pair for delivering ablative energy, e.g., via irreversible electroporation as further described herein. The inflatable member (1906) can be formed of an insulating material and, as orientated and shaped, can direct the electric field generated by the electrodes (1909, 1911) toward the wall (1902) of the pulmonary vein ostium (1901).

Each of the ablation devices (110, 200, 300, 400, 500, 600, 700, 800, 900, 1800, 1900, etc.) described herein may include a handle (not shown) that may, in some embodiments, be coupled to a proximal portion of the ablation device and may include a mechanism (not shown) (e.g., knob, switch, pull wires) configured to modify the location of the second electrode relative to the first electrode. For example, the first electrode and the second electrode may be brought closer together by retracting the second catheter or guidewire lumen relative to the first catheter. In some embodiments, the first catheter may have a deflectable portion proximal to the proximal electrode whose shape is controlled by a steering knob or other control on the catheter handle. In embodiments, the device is tracked over a guidewire positioned in a pulmonary vein through a steerable sheath, and deflection of the sheath can provide steering control for positioning the guidewire and inflatable member of the ablation catheter in a pulmonary vein. The inflatable member may be inflated through a fluid port attached to the catheter handle wherein distilled or deionized water can be infused under pressure. In this manner, apposition of the ablation device to tissue may be provided at a desired position and orientation (e.g., at a pulmonary vein ostium).

The ablation devices described herein may be useful for forming lesions on endocardial surfaces, such as an inner surface of a pulmonary vein, as described herein. A distal portion of the inflatable member may include and/or be formed in an atraumatic shape that reduces trauma to tissue (e.g., prevents and/or reduces the possibility of tissue puncture). The inflatable member may be sized for advancement into an endocardial space. A set of electrical leads and/or a fluid (e.g., saline) may be disposed within the lumen of the first catheter.

In some embodiments, the electrodes may be shaped to conform to the shape of the catheter upon which they are disposed. For example, the electrodes may be press fit (e.g., crimped) to a first catheter or outer shaft, or attached using an adhesive with electrical leads attached to the electrodes. The first catheter may include flexible portions (e.g., may be deflectable) to enhance flexibility and allow the device to be deflected.

Each of the electrodes of any of the ablation devices discussed herein may be connected to an insulated electrical lead (not shown) leading to a handle (not shown) coupled to a proximal portion of the first catheter. The insulation on each of the electrical leads may sustain an electrical potential difference of at least 700 V across its thickness without dielectric breakdown. In other embodiments, the insulation on each of the electrical leads may sustain an electrical potential difference of between about 200 V to about 3,000 V across its thickness without dielectric breakdown, including all values and sub-ranges in between. This allows the electrodes and inflatable member coupled thereto to effectively deliver electrical energy and to ablate tissue through irreversible electroporation. The electrodes may, for example, receive pulse waveforms generated by a signal generator (122) as discussed above with respect to FIG. 1.

For each of the ablation devices discussed herein, the electrodes may include biocompatible metals such as titanium, palladium, gold, silver, platinum or a platinum alloy. For example, the electrode may preferably include platinum or a platinum alloy. In some embodiments, the proximal electrodes may have a biocompatible coating that permits capacitive voltage delivery with biphasic waveforms. Each electrode may include an electrical lead having sufficient electrical insulation to sustain an electrical potential difference of at least 700 V across its thickness without dielectric breakdown. In other embodiments, the insulation on each of the electrical leads may sustain an electrical potential difference of between about 200 V to about 3,000 V across its thickness without dielectric breakdown, including all values and sub-ranges in between. The insulated electrical leads may run to the proximal handle portion of the ablation device from where they may be connected to a suitable electrical connector. The first catheter may be made of a flexible polymeric material such as Teflon, Nylon, Pebax, etc.

In some embodiments, the inflatable members as described herein may have an expandable structure and may be composed of any of a variety of insulating or dielectric materials including, but not limited to polyvinyl chloride (PVC), polyethylene (PE), cross-linked polyethylene, polyolefins, polyolefin copolymer (POC), polyethylene terephthalate (PET), polyester, nylon, polymer blends, polyester, polyimide, polyamides, polyurethane, silicone, polydimethylsiloxane (PDMS), PEBAX, and the like. Preferred embodiments can be composed of polyurethane or silicone. Together with the use of distilled or deionized water to inflate the inflatable member, the inflatable member serves as an effective insulator during delivery of the Pulsed Electric Field waveform and drives the electric field to the region outside the inflatable member or balloon and surrounding the balloon.

II. Methods

Also described here are methods for ablating tissue in a pulmonary vein (e.g., pulmonary vein in the left atrium) using the systems and devices described above. Generally, the methods described here include introducing and disposing a device in an ostium of a pulmonary vein. A pulse waveform may be delivered by one or more electrodes and an inflatable member (e.g., balloon) of the device to ablate tissue. In some embodiments, a cardiac pacing signal may synchronize the delivered pulse waveforms with the cardiac cycle. Additionally or alternatively, the pulse waveforms may include a plurality of levels of a hierarchy to reduce total energy delivery. The tissue ablation thus performed may be delivered in synchrony with paced heartbeats and with less energy delivery to reduce damage to healthy tissue. It should be appreciated that any of the ablation devices described herein may be used to ablate tissue using the methods discussed below as appropriate.

Figure 20A:
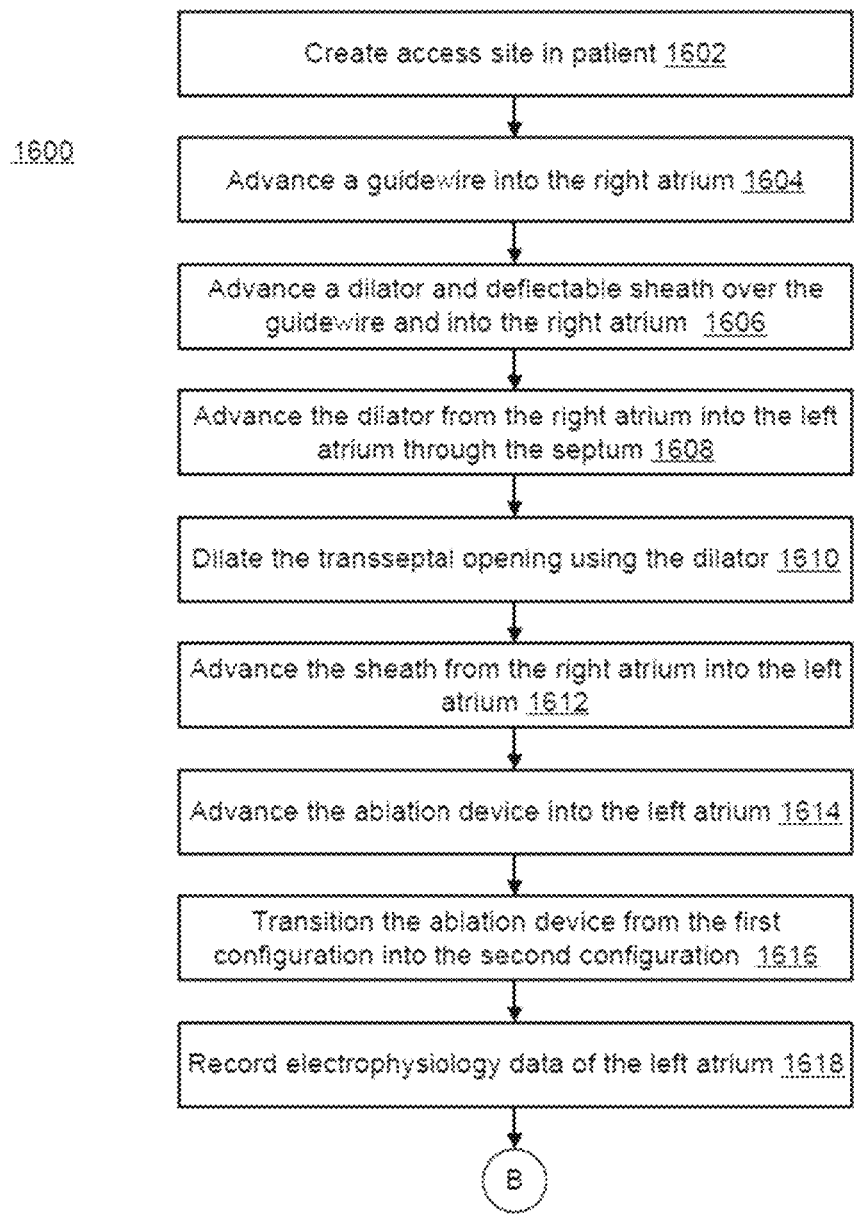
FIGS. 20A-20B illustrates a method for tissue ablation, according to embodiments.
Figure 20B:
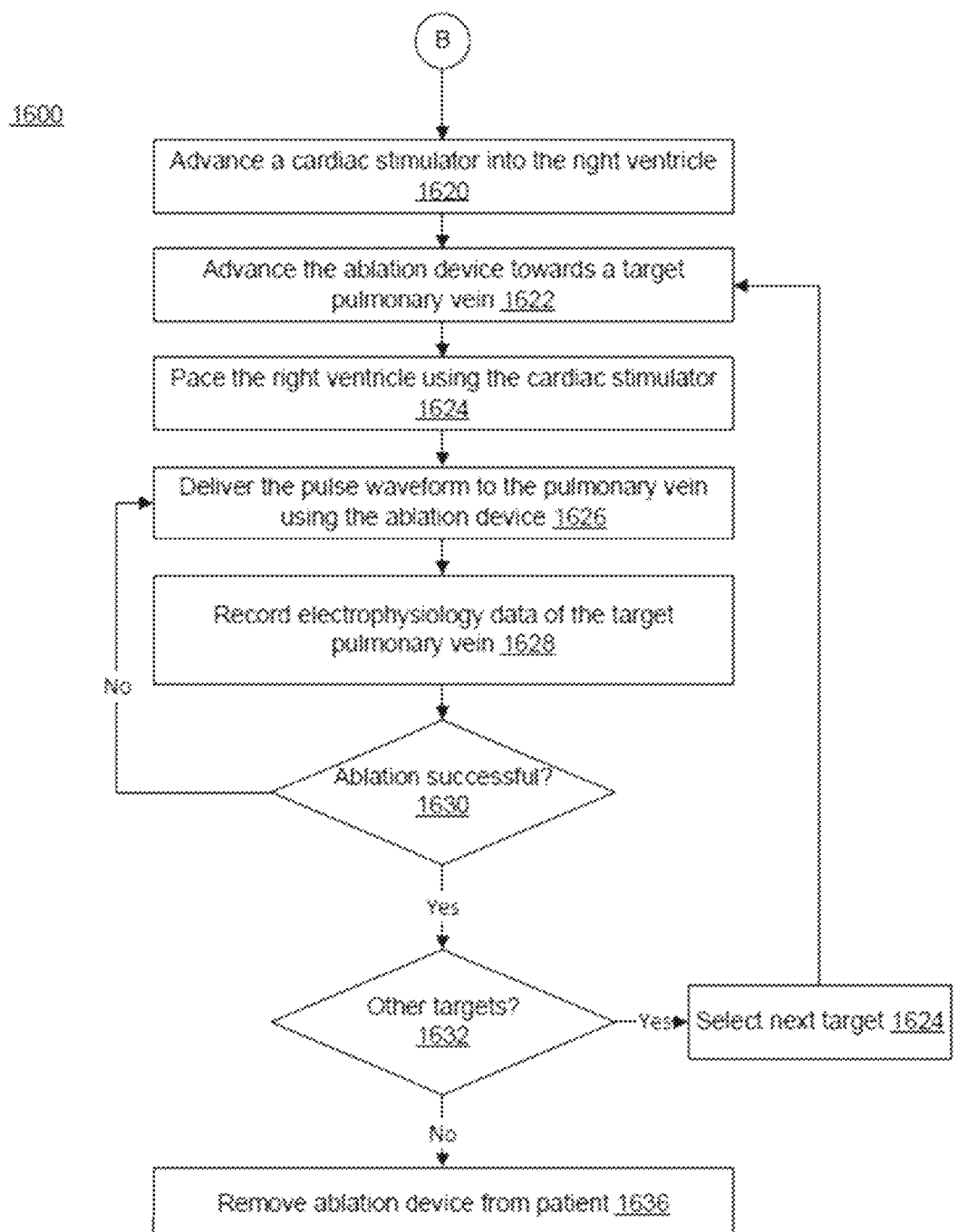

Generally, and as illustrated in FIGS. 20A-20B, a method (1600) includes the introduction of a device (e.g., ablation device, such as the ablation devices (110, 200, 300, 400, 500, 600, 700, 800, 900) into an endocardial space of a pulmonary vein. The ablation device may be introduced in a first or deflated configuration and transitioned to a second or inflated configuration in an ostium of a pulmonary vein. Once positioned, voltage pulse waveforms may be applied to tissue during a refractory period of the cardiac cycle. Electrophysiology data of the cardiac chamber may be recorded to determine efficacy of the ablation.

The method (1600) may begin with creating an access site in a patient (1602). For example, a first access site may be via a femoral vein of the patient. A guidewire may be advanced into the access site via the femoral vein and into the right atrium of the patient (1604). A dilator and a deflectable sheath may be advanced over the guidewire and into the right atrium (1606). The sheath may, for example, be configured for deflecting up to about 180 degrees or more. The dilator may be advanced from the right atrium into the left atrium through the septum (1608) to create a transseptal opening. For example, the dilator may be advanced from the right atrium into the left atrium through the interatrial septum to create the transseptal opening. The interatrial septum may include the fossa ovalis of the patient. The transseptal opening may be dilated using the dilator (1610). For example, the dilator may be advanced out of the sheath and used to puncture the fossa ovalis to create the transseptal opening (assuming the patient is heparinized). Alternatively, a transseptal needle (e.g., Brockenbrough needle) may be used to create the transseptal opening. The sheath may be advanced from the right atrium into the left atrium (1612) through the transseptal opening. An ablation device may be advanced into the left atrium over the guidewire (1614), with the second catheter or guidewire lumen of the ablation device tracking over the guidewire.

In some embodiments, the ablation device may include a catheter lumen and a set of insulated electrical leads extending through the lumen. In embodiments, a thin microcatheter with a circular distal shape with electrodes mounted on the circular shape may be introduced through the second catheter or guidewire lumen into the pulmonary vein, and used to record intracardiac ECG data to confirm successful ablation.

Still referring to FIGS. 20A-20B, a second access site may be created in the patient to advance a lead or catheter for cardiac stimulation into the patient's heart. For example, the second access site may be via a jugular vein of the patient. The device for cardiac stimulation may be advanced into the right ventricle through the second access site (1620) (e.g., near the apex of the right ventricle). A pacing signal may be generated by a cardiac stimulator and applied to the heart for cardiac stimulation of the heart. An indication of the pacing signal may be transmitted from the cardiac stimulator to the signal generator. In some embodiments, the operator may confirm the pacing capture and determine that the ventricle is responding to the pacing signal as intended. For example, pacing capture may be confirmed on an ECG display on a signal generator. Confirmation of pacing capture is a safety feature in that ablation is delivered in synchrony with pacing through enforced periodicity of a Q-wave through pacing. Likewise, in some embodiments, an additional pacing catheter may be used for example to pace the right atrium in addition to the right ventricle, and ablation can be delivered during the common refractory window of both cardiac chambers.

The ablation device may be advanced towards a target pulmonary vein (1622) for delivering a pulse waveform configured for tissue ablation. In particular, the ablation device in the second configuration may be advanced towards a pulmonary vein of the heart to engage tissue surface. The sheath may be deflected as needed to direct the ablation device towards the target vein. The inflatable member may be transitioned to a second configuration where the inflatable member inflates to contact the inflatable member against the pulmonary vein. Once the ablation device is in position within the heart to deliver one or more pulse waveforms, an extension cable may be used to electrically couple a signal generator to a proximal end of the handle of the ablation device. After pacing the right ventricle using the pacing device (1624), the pulse waveform may be delivered to the target site using the ablation device to ablate tissue. The pulse waveform may be delivered in synchronization with the pacing signal.

While examples of ablation devices configured for delivery of irreversible electroporation pulsed electric field therapy have been described here, the examples described herein are provided for exemplary purposes only and those skilled in the art may devise other variations without departing from the scope of the present invention. For example, a range and variety of materials, polyhedral sides, electrode diameters, device dimensions, voltage levels, proximal electrodes, and other such details are possible and may be implemented as convenient for the application at hand without departing from the scope of the present invention. In embodiments where the distal shaft of the catheter is deflectable, the catheter shaft may undergo a range of deflections by controlling deflection from a catheter handle.

As discussed herein, the pulse waveform may be generated by a signal generator coupled to the ablation device. The signal generator may be electrically coupled to a proximal end of a handle of the ablation device. For example, an extension cable may electrically couple the signal generator to the proximal end of the handle. In some embodiments, the pulse waveform may include a time offset with respect to the pacing signal. In some embodiments, the pulse waveform may include a first level of a hierarchy of the pulse waveform including a first set of pulses. Each pulse has a pulse time duration and a first time interval separating successive pulses. A second level of the hierarchy of the pulse waveform may include a plurality of first sets of pulses as a second set of pulses. A second time interval may separate successive first sets of pulses. The second time interval may be at least three times the duration of the first time interval. A third level of the hierarchy of the pulse waveform may include a plurality of second sets of pulses as a third set of pulses. A third time interval may separate successive second sets of pulses. The third time interval may be at least thirty times the duration of the second level time interval. A fourth level of the hierarchy of the pulse waveform may include a plurality of third sets of pulses as a fourth set of pulses. A fourth time interval may separate successive third sets of pulses. The fourth time interval may be at least ten times the duration of the third level time interval.

In other embodiments, the ablation device may be withdrawn from the heart over the guidewire and a mapping catheter may be advanced over the guidewire to record the post-ablation electrophysiology data of the target site. If the ablation is not successful (1630—NO) based on the electrophysiology data and predetermined criteria, then the process may return to step 1626 for delivery of additional pulse waveforms. The pulse waveform parameters may be the same or changed for subsequent ablation cycles.

If analysis of the electrophysiology data indicates that the ablation is successful (e.g., tissue portion is electrically silent) (1630—YES), then a determination may be made of other target portions to ablate (1632) (e.g., other pulmonary veins). Another target portion may be selected (1624) and the process may return to step 1622 when other portions are to be ablated. When switching between target tissue, the inflatable member may be at least partially deflated, and the ablation device may be advanced towards another portion of tissue. If no other portions are to be ablated (1632—NO), the ablation device, pacing catheters, sheath, guidewire, and the like, may be removed from the patient (1636).

It should be noted that for any of the steps described herein, a radiopaque portion of the ablation device may be fluoroscopically imaged to aid an operator. For example, visual confirmation may be performed through fluoroscopic imaging that the inflatable members in the second configuration is in contact with and approximately centered in a vein, by means of a radio-opaque marker band placed on the distal portion of the device.

It should be understood that the examples and illustrations in this disclosure serve exemplary purposes and departures and variations such as inflatable member characteristics, number of electrodes, and so on can be built and deployed according to the teachings herein without departing from the scope of this invention.

Pulse Waveform

Disclosed herein are methods, systems and apparatuses for the selective and rapid application of pulsed electric fields/waveforms to effect tissue ablation with irreversible electroporation. The pulse waveform(s) as disclosed herein are usable with any of the systems (100), devices (e.g., 200, 300, 400, 500, 600, 700, 800, 900), and methods (e.g., 1600) described herein. Some embodiments are directed to pulsed high voltage waveforms together with a sequenced delivery scheme for delivering energy to tissue via sets of electrodes. In some embodiments, peak electric field values can be reduced and/or minimized while at the same time sufficiently large electric field magnitudes can be maintained in regions where tissue ablation is desired. In some embodiments, a system useful for irreversible electroporation includes a signal generator and a processor capable of being configured to apply pulsed voltage waveforms to a selected plurality or a subset of electrodes of an ablation device. In some embodiments, the processor is configured to control inputs whereby selected pairs of anode-cathode subsets of electrodes can be either simultaneously or sequentially triggered based on a pre-determined sequence, and in one embodiment the sequenced delivery can be triggered from a cardiac stimulator and/or pacing device. In some embodiments, the ablation pulse waveforms are applied in a refractory period of the cardiac cycle so as to avoid disruption of the sinus rhythm of the heart. One example method of enforcing this is to electrically pace the heart with a cardiac stimulator and ensure pacing capture to establish periodicity and predictability of the cardiac cycle, and then to define a time window well within the refractory period of this periodic cycle within which the ablation waveform is delivered.

In some embodiments, the pulsed voltage waveforms disclosed herein are hierarchical in organization and have a nested structure. In some embodiments, the pulsed waveform includes hierarchical groupings of pulses with a variety of associated timescales. Furthermore, the associated timescales and pulse widths, and the numbers of pulses and hierarchical groupings, can be selected so as to satisfy one or more of a set of Diophantine inequalities involving the frequency of cardiac pacing.

Pulsed waveforms for electroporation energy delivery as disclosed herein may enhance the safety, efficiency and effectiveness of the energy delivery by reducing the electric field threshold associated with irreversible electroporation, yielding more effective ablative lesions with reduced total energy delivered.

Figure 15:
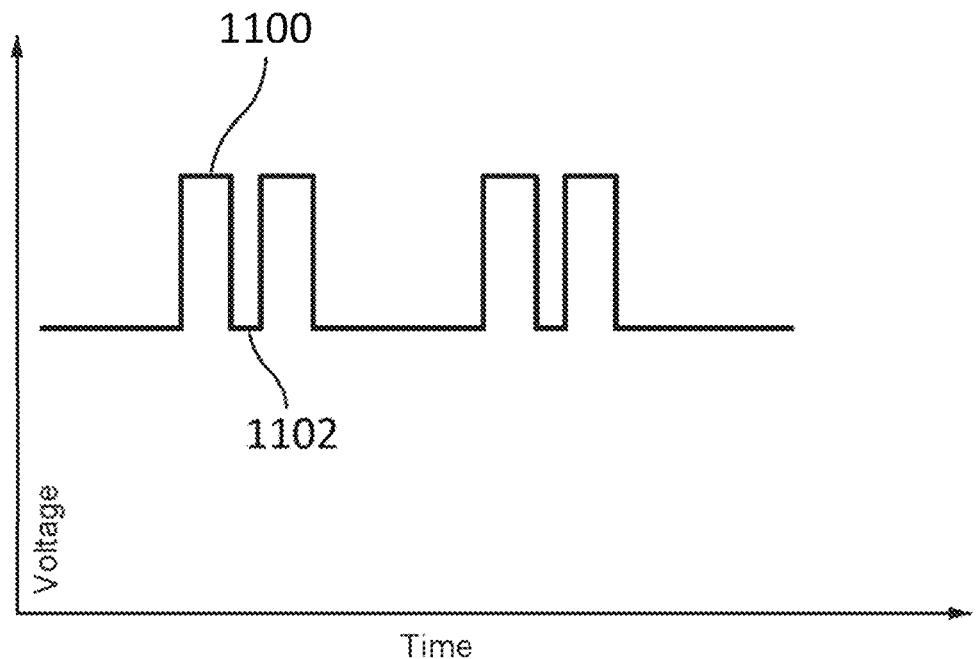
FIG. 15 is an example waveform showing a sequence of voltage pulses with a pulse width defined for each pulse, according to embodiments.

FIG. 15 illustrates a pulsed voltage waveform in the form of a sequence of rectangular double pulses, with each pulse, such as the pulse (1100) being associated with a pulse width or duration. The pulse width/duration can be about 0.5 microseconds, about 1 microsecond, about 5 microseconds, about 10 microseconds, about 25 microseconds, about 50 microseconds, about 100 microseconds, about 125 microseconds, about 140 microseconds, about 150 microseconds, including all values and sub-ranges in between. The pulsed waveform of FIG. 15 illustrates a set of monophasic pulses where the polarities of all the pulses are the same (all positive in FIG. 15, as measured from a zero baseline). In some embodiments, such as for irreversible electroporation applications, the height of each pulse (1100) or the voltage amplitude of the pulse (1100) can be in the range from about 400 volts, about 1,000 volts, about 5,000 volts, about 10,000 volts, about 15,000 volts, including all values and sub ranges in between. As illustrated in FIG. 15, the pulse (1100) is separated from a neighboring pulse by a time interval (1102), also sometimes referred to as a first time interval. As examples, the first time interval can be about 1 microsecond, about 50 microseconds, about 100 microseconds, about 200 microseconds, about 500 microseconds, about 800 microseconds, about 1 millisecond including all values and sub ranges in between, in order to generate irreversible electroporation.

Figure 16:
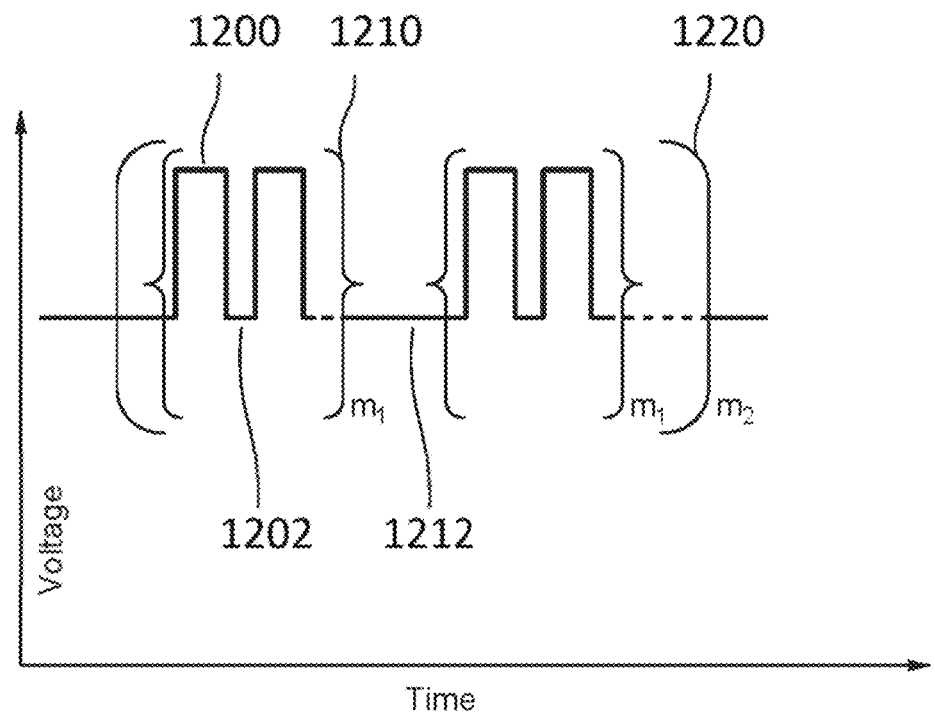
FIG. 16 schematically illustrates a hierarchy of pulses showing pulse widths, intervals between pulses, and groupings of pulses, according to embodiments.

FIG. 16 introduces a pulse waveform with the structure of a hierarchy of nested pulses. FIG. 16 shows a series of monophasic pulses such as pulse (1200) with pulse width/pulse time duration w, separated by a time interval (also sometimes referred to as a first time interval) such as (1202) of duration t1 between successive pulses, a number m1 of which are arranged to form a group of pulses (1210) (also sometimes referred to as a first set of pulses). Furthermore, the waveform has a number m2 of such groups of pulses (also sometimes referred to as a second set of pulses) separated by a time interval (1212) (also sometimes referred to as a second time interval) of duration t2 between successive groups. The collection of m2 such pulse groups, marked by (1220) in FIG. 16, constitutes the next level of the hierarchy, which can be referred to as a packet and/or as a third set of pulses. The pulse width and the time interval t1 between pulses can both be in the range of microseconds to hundreds of microseconds, including all values and sub ranges in between. In some embodiments, the time interval t2 can be at least three times larger than the time interval t1. In some embodiments, the ratio t2/t1 can be in the range between about 3 and about 300, including all values and sub-ranges in between.

Figure 17:
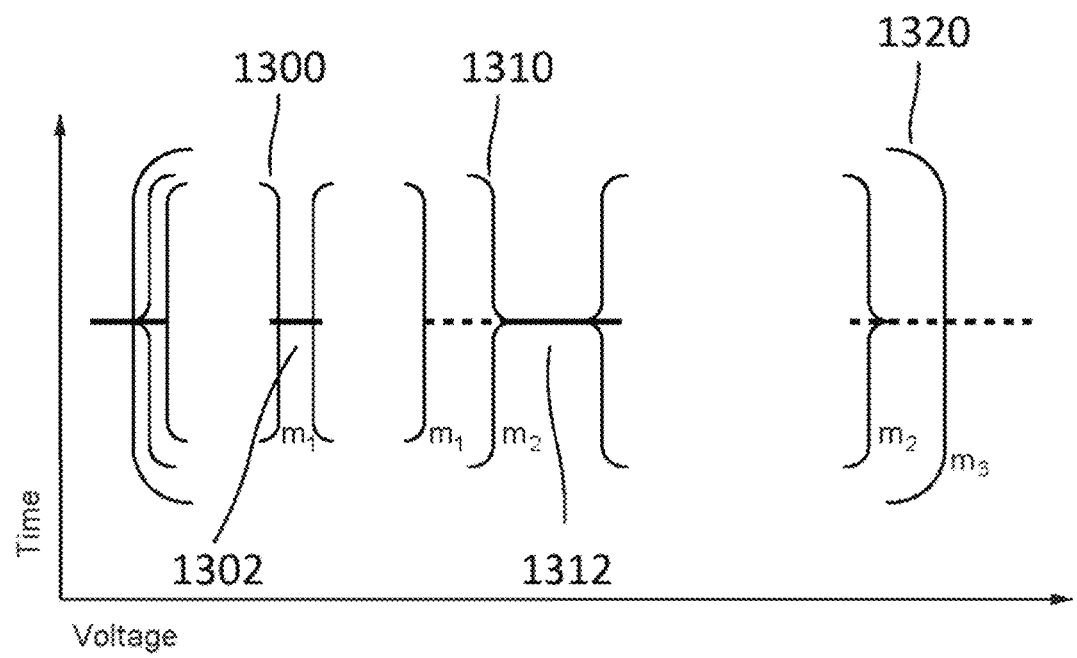
FIG. 17 provides a schematic illustration of a nested hierarchy of monophasic pulses displaying different levels of nested hierarchy, according to embodiments.

FIG. 17 further elaborates the structure of a nested pulse hierarchy waveform. In this figure, a series of m1 pulses (individual pulses not shown) form a group of pulses (1300) (e.g., a first set of pulses). A series of m2 such groups separated by an inter-group time interval (1310) of duration t2 (e.g., a second time interval) between one group and the next form a packet (e.g., a second set of pulses). A series of m3 such packets separated by time intervals (1312) of duration t3 (e.g., a third time interval) between one packet and the next form the next level in the hierarchy, a super-packet labeled (1320) (e.g., a third set of pulses) in the figure. In some embodiments, the time interval t3 can be at least about thirty times larger than the time interval t2. In some embodiments, the time interval t3 can be at least fifty times larger than the time interval t2. In some embodiments, the ratio t3/t2 can be in the range between about 30 and about 800, including all values and sub-ranges in between. The amplitude of the individual voltage pulses in the pulse hierarchy can be anywhere in the range from 500 volts to 7,000 volts or higher, including all values and sub ranges in between.

Figure 18:
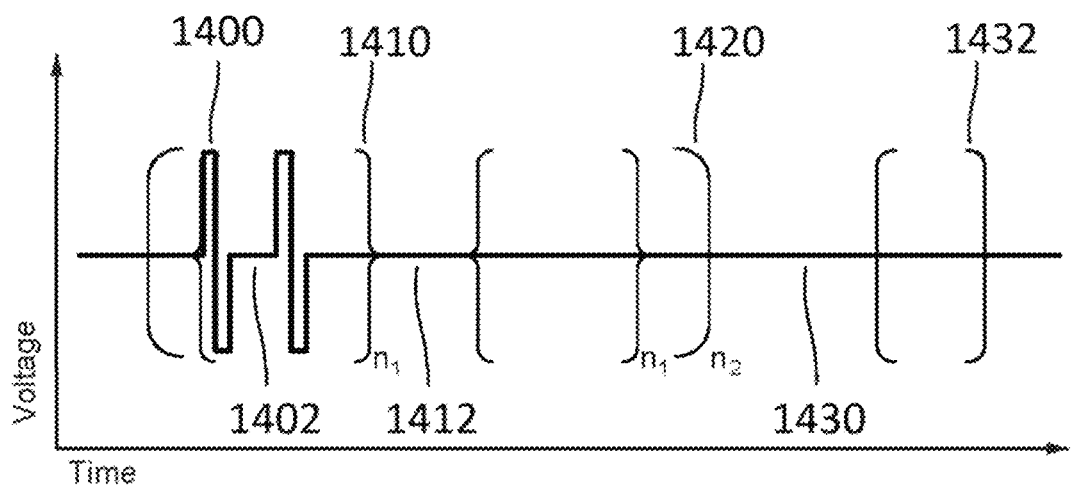
FIG. 18 is a schematic illustration of a nested hierarchy of biphasic pulses displaying different levels of nested hierarchy, according to embodiments.

FIG. 18 provides an example of a biphasic waveform sequence with a hierarchical structure. In the example shown in the figure, biphasic pulses such as (1400) have a positive voltage portion as well as a negative voltage portion to complete one cycle of the pulse. There is a time delay (1402) (e.g., a first time interval) between adjacent cycles of duration t1, and n1 such cycles form a group of pulses (1410) (e.g., a first set of pulses). A series of n2 such groups separated by an inter-group time interval (1412) (e.g., a second time interval) of duration t2 between one group and the next form a packet (1420) (e.g., a second set of pulses). The figure also shows a second packet (1430), with a time delay (1432) (e.g., a third time interval) of duration t3 between the packets. Just as for monophasic pulses, higher levels of the hierarchical structure can be formed as well. The amplitude of each pulse or the voltage amplitude of the biphasic pulse can be anywhere in the range from 500 volts to 7,000 volts or higher, including all values and sub ranges in between. The pulse width/pulse time duration can be in the range from nanoseconds or even sub-nanoseconds to tens of microseconds, while the delays t1 can be in the range from zero to several microseconds. The inter-group time interval t2 can be at least ten times larger than the pulse width. In some embodiments, the time interval t3 can be at least about twenty times larger than the time interval t2. In some embodiments, the time interval t3 can be at least fifty times larger than the time interval t2.

Embodiments disclosed herein include waveforms structured as hierarchical waveforms that include waveform elements/pulses at various levels of the hierarchy. The individual pulses such as (1200) in FIG. 16 comprise the first level of the hierarchy, and have an associated pulse time duration and a first time interval between successive pulses. A set of pulses, or elements of the first level structure, form a second level of the hierarchy such as the group of pulses/second set of pulses (1210) in FIG. 16. Among other parameters, associated with the waveform are parameters such as a total time duration of the second set of pulses (not shown), a total number of first level elements/first set of pulses, and second time intervals between successive first level elements that describe the second level structure/second set of pulses. In some embodiments, the total time duration of the second set of pulses can be between about 20 microseconds and about 10 milliseconds, including all values and subranges in between. A set of groups, second set of pulses, or elements of the second level structure, form a third level of the hierarchy such as the packet of groups/third set of pulses (1220) in FIG. 16. Among other parameters, there is a total time duration of the third set of pulses (not shown), a total number of second level elements/second set of pulses, and third time intervals between successive second level elements that describe the third level structure/third set of pulses. The generally iterative or nested structure of the waveforms can continue to a higher plurality of levels, such as ten levels of structure, or more.

For example, a pulse waveform may include a fourth level of the hierarchy of the pulse waveform may include a plurality of third sets of pulses as a fourth set of pulses, a fourth time interval separating successive third sets of pulses, the fourth time interval being at least ten times the duration of the third level time interval.

In some embodiments, hierarchical waveforms with a nested structure and hierarchy of time intervals as described herein are useful for irreversible electroporation ablation energy delivery, providing a good degree of control and selectivity for applications in different tissue types. A variety of hierarchical waveforms can be generated with a suitable pulse generator. It is understood that while the examples herein identify separate monophasic and biphasic waveforms for clarity, it should be noted that combination waveforms, where some portions of the waveform hierarchy are monophasic while other portions are biphasic, can also be generated/implemented.

Figure 19:
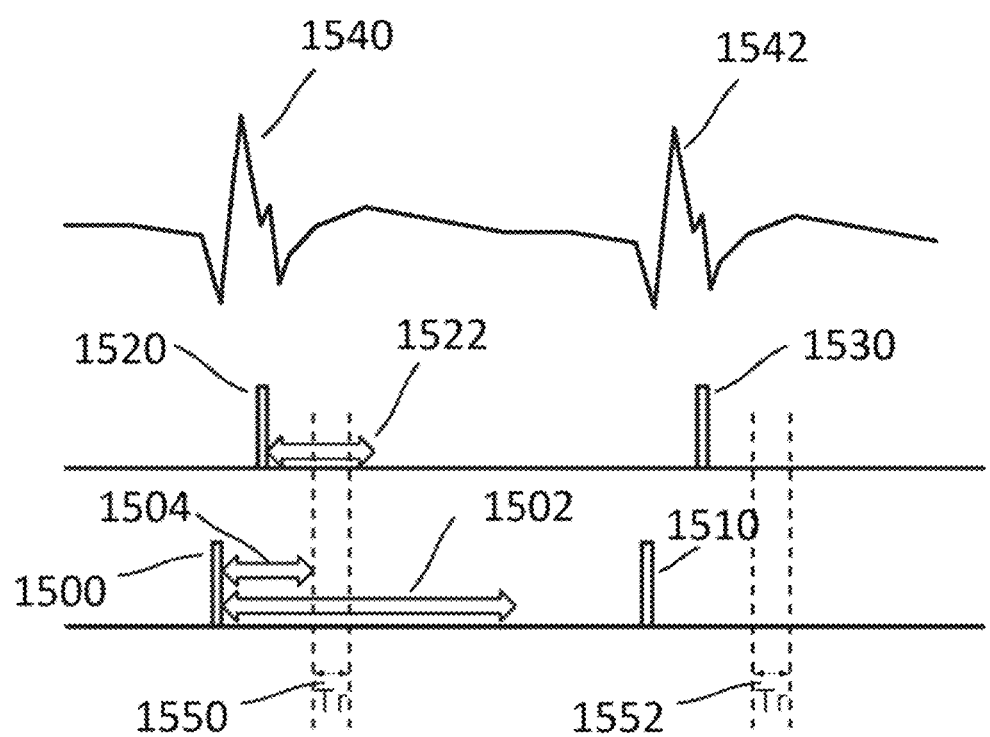
FIG. 19 illustrates schematically a time sequence of electrocardiograms and cardiac pacing signals together with atrial and ventricular refractory time periods and indicating a time window for irreversible electroporation ablation, according to embodiments.

In some embodiments, the ablation pulse waveforms described herein are applied during the refractory period of the cardiac cycle so as to avoid disruption of the sinus rhythm of the heart. In some embodiments, a method of treatment includes electrically pacing the heart with a cardiac stimulator to ensure pacing capture to establish periodicity and predictability of the cardiac cycle, and then defining a time window within the refractory period of the cardiac cycle within which one or more pulsed ablation waveforms can be delivered. FIG. 19 illustrates an example where both atrial and ventricular pacing is applied (for instance, with pacing leads or catheters situated in the right atrium and right ventricle respectively). With time represented on the horizontal axis, FIG. 19 illustrates a series of ventricular pacing signals such as (1500) and (1510), and a series of atrial pacing signals (1520, 1530), along with a series of ECG waveforms (1540, 1542) that are driven by the pacing signals. As indicated in FIG. 19 by the thick arrows, there is an atrial refractory time window (1522) and a ventricular refractory time window (1502) that respectively follow the atrial pacing signal (1522) and the ventricular pacing signal (1500). As shown in FIG. 19, a common refractory time window (1550) of duration Tr can be defined that lies within both atrial and ventricular refractory time windows (1522, 1502). In some embodiments, the electroporation ablation waveform(s) can be applied in this common refractory time window (1550). The start of this refractory time window (1522) is offset from the pacing signal (1500) by a time offset (1504) as indicated in FIG. 19. The time offset (1504) can be smaller than about 25 milliseconds, in some embodiments. At the next heartbeat, a similarly defined common refractory time window (1552) is the next time window available for application of the ablation waveform(s). In this manner, the ablation waveform(s) may be applied over a series of heartbeats, at each heartbeat remaining within the common refractory time window. In one embodiment, each packet of pulses as defined above in the pulse waveform hierarchy can be applied over a heartbeat, so that a series of packets is applied over a series of heartbeats, for a given electrode set.

As used herein, the terms "about" and/or "approximately" when used in conjunction with numerical values and/or ranges generally refer to those numerical values and/or ranges near to a recited numerical value and/or range. In some instances, the terms "about" and "approximately" may mean within ±10% of the recited value. For example, in some instances, "about 100 [units]" may mean within ±10% of 100 (e.g., from 90 to 110). The terms "about" and "approximately" may be used interchangeably.

Some embodiments described herein relate to a computer storage product with a non-transitory computer-readable medium (also may be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also may be referred to as code or algorithm) may be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which may include, for example, the instructions and/or computer code disclosed herein.

The systems, devices, and/or methods described herein may be performed by software (executed on hardware), hardware, or a combination thereof. Hardware modules may include, for example, a general-purpose processor (or microprocessor or microcontroller), a field programmable gate array (FPGA), and/or an application specific integrated circuit (ASIC). Software modules (executed on hardware) may be expressed in a variety of software languages (e.g., computer code), including C, C++, Java®, Ruby, Visual Basic®, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. Additional examples of computer code include, but are not limited to, control signals, encrypted code, and compressed code.

The specific examples and descriptions herein are exemplary in nature and embodiments may be developed by those skilled in the art based on the material taught herein without departing from the scope of the present invention, which is limited only by the attached claims.

We claim:

1. An apparatus, comprising:
a first shaft having a longitudinal axis and defining a lumen;
a second shaft disposed within the lumen and having a distal portion that extends from a distal portion of the first shaft, the second shaft moveable along the longitudinal axis relative to the first shaft;
a first electrode coupled to the distal portion of the first shaft;
a second electrode coupled to the distal portion of the second shaft, the first and second electrodes configured to generate an electric field for ablating tissue; and
an inflatable member disposed between the first and second electrodes, the inflatable member configured to transition from an undeployed configuration to a deployed configuration in response to the second shaft being moved proximally relative to the first shaft, the inflatable member in the deployed configuration having a conical shape configured to engage a wall of a pulmonary vein ostium and direct the electric field generated by the first and second electrodes toward the wall.

2. The apparatus of claim 1, wherein the inflatable member includes a wall having:
a proximal portion;
a distal portion; and
a middle portion disposed between the proximal and distal portions of the wall, the middle portion having a minimum thickness that is less than a thickness of the proximal and distal portions of the wall.

3. The apparatus of claim 2, wherein a length of each of the proximal and distal portions of the inflatable member along the longitudinal axis is greater than a length of the middle portion of the wall along the longitudinal axis.

4. An apparatus, comprising:
a shaft having a longitudinal axis and defining a lumen;
an inflatable member disposed near a distal portion of the shaft, the inflatable member configured to transition between an undeployed configuration and a deployed configuration, the inflatable member including a wall having a proximal portion, a distal portion, and a middle portion disposed between the proximal and distal portions of the wall, the middle portion having a minimum thickness that is less than a thickness of the proximal and distal portions of the wall; and
a proximal first electrode and a distal second electrode disposed on opposite sides of the inflatable member along the longitudinal axis, the first and second electrodes configured to generate an electric field for ablating tissue, wherein in the deployed configuration the distal portion of the wall extends from the middle portion of the wall toward first electrode.

5. The apparatus of claim 4, wherein the inflatable member in the deployed configuration is configured to engage a wall of a pulmonary vein ostium, the inflatable member formed of an insulating material such that the inflatable member in the deployed configuration directs the electric field generated by the first and second electrodes toward the wall of the pulmonary vein ostium.

6. The apparatus of claim 4, wherein the inflatable member in the deployed configuration includes at least a proximal portion or a distal portion that is angled greater than about 45 degrees relative to the longitudinal axis.

7. The apparatus of claim 4, wherein the minimum thickness of the middle portion is less than about a third of the thickness of at least the proximal or distal portion of the wall.

8. The apparatus of claim 4, wherein a ratio of the length of the proximal portion to the length of the middle portion and a ratio of the length of the distal portion to the length of the middle portion are greater than about three.

9. The apparatus of claim 4, wherein the inflatable member in the deployed configuration has a cross-sectional shape having a width of less than about 40 mm, a height of less than about 25 mm, and a side portion with a radius of curvature of less than about 15 mm.

10. The apparatus of claim 4, wherein the inflatable member in the deployed configuration has a cross-sectional shape having a maximum width of between about 20 mm and about 40 mm.

11. The apparatus of claim 4, wherein the first electrode is attached to a proximal portion of the inflatable member and the second electrode is attached to a distal portion of the inflatable member.

12. The apparatus of claim 4, wherein each of the first and second electrodes has an outer diameter of about 1 mm to 7 mm and a length along the longitudinal axis of about 1 mm to about 15 mm.

13. The apparatus of claim 4, wherein the second electrode has a rounded distal end.

14. The apparatus of claim 4, wherein a length of each of the proximal and distal portions of the inflatable member along the longitudinal axis is greater than a length of the middle portion along the longitudinal axis.

15. The apparatus of claim 4, wherein the inflatable member is fluidically coupled to an infusion device, the inflatable member configured to transition from the undeployed configuration to the deployed configuration in response to an infusion of fluid from the infusion device.

16. The apparatus of claim 15, wherein the infusion of fluid is delivered at an infusion pressure of between about 2 psi and about 20 psi.

17. A system, comprising:
a signal generator configured to generate a pulse waveform;
an ablation device coupled to the signal generator, the ablation device including:
first and second electrodes configured to receive the pulse waveform and generate an electric field for ablation; and
an inflatable member formed of an insulating material and disposed between the first and second electrodes, the inflatable member configured to transition between an undeployed configuration in which the inflatable member can be advanced to a pulmonary vein ostium to a deployed configuration having a conical shape in which the inflatable member can engage with a wall of the pulmonary vein ostium, the inflatable member in the deployed configuration configured to direct the electric field toward the wall.

18. The system of claim 17, wherein the ablation device further includes:
a first shaft having a longitudinal axis and defining a lumen; and
a second shaft extending through the lumen, the second shaft movable relative to the first shaft to bring proximal and distal ends of the inflatable member along the longitudinal axis closer to one another to transition the inflatable member from the undeployed state into the deployed state.

19. The system of claim 18, further comprising a handle coupled to a proximal portion of the ablation device, the handle including a mechanism configured to move the second shaft relative to the first shaft.

20. The system of claim 19, wherein the handle further includes a locking mechanism configured to lock a position of the second shaft relative to the first shaft to maintain the inflatable member in the deployed configuration.

* * * * *